United States Patent
Elsohly et al.

(10) Patent No.: US 9,630,941 B2
(45) Date of Patent: Apr. 25, 2017

(54) COMPOSITIONS CONTAINING DELTA-9-THC-AMINO ACID ESTERS AND PROCESS OF PREPARATION

(71) Applicant: The University of Mississippi, University, MS (US)

(72) Inventors: Mahmoud A. Elsohly, Oxford, MS (US); Waseem Gul, Oxford, MS (US); Michael A. Repka, Oxford, MS (US); Soumyajit Majumdar, Oxford, MS (US); Mohammad Khalid Ashfaq, Oxford, MS (US)

(73) Assignee: The University of Mississippi, University, MS (US)

( * ) Notice: Subject to any disclaimer, the term of this patent is extended or adjusted under 35 U.S.C. 154(b) by 84 days.

(21) Appl. No.: 14/462,482

(22) Filed: Aug. 18, 2014

(65) Prior Publication Data

US 2015/0045282 A1 Feb. 12, 2015

Related U.S. Application Data

(63) Continuation-in-part of application No. 13/126,606, filed as application No. PCT/US2009/062998 on Nov. 2, 2009, now Pat. No. 8,809,261.
(Continued)

(51) Int. Cl.
*A61K 38/00* (2006.01)
*C07D 311/80* (2006.01)
(Continued)

(52) U.S. Cl.
CPC ............ *C07D 311/80* (2013.01); *A61K 9/006* (2013.01); *A61K 9/0048* (2013.01);
(Continued)

(58) Field of Classification Search
None
See application file for complete search history.

(56) References Cited

U.S. PATENT DOCUMENTS 5,389,375 A * 2/1995 Elsohly .......................... 424/436
5,631,297 A * 5/1997 Pate et al. ..................... 514/627
(Continued)

FOREIGN PATENT DOCUMENTS

WO    WO 2009/026461    *   2/2009
WO    WO 2009/051819    *   4/2009

OTHER PUBLICATIONS

Cavalli et al, Solid lipid nanoparticles (SLN) as ocular delivery system for tobramycin (International Journal of Pharmaceutics 238 (2002) 241-245).*

*Primary Examiner* — James H Alstrum Acevedo
*Assistant Examiner* — Sergio Coffa
(74) *Attorney, Agent, or Firm* — Hershkovitz & Associates, PLLC; Abraham Hershkovitz; Eugene C. Rzucidlo

(57) ABSTRACT

Suppository, hot melt and ophthalmic formulations containing amino esters of the formulae (I), (II) and (III), where R1, R2 and R3 are residues of amino acids such as, but not limited to, valine, sarcosine, leucine, glutamine, tryptophan, tyrosine, alanine and 4(4-aminophenyl)butyric acid or combination thereof, and salts thereof.

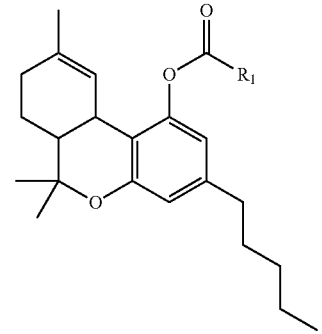

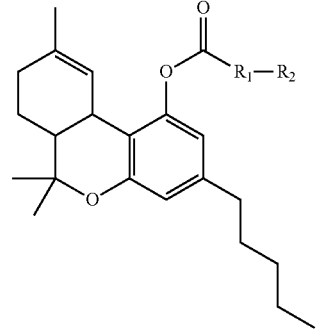

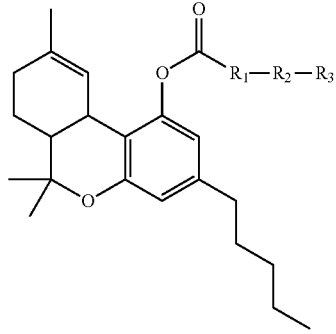

23 Claims, 22 Drawing Sheets

Related U.S. Application Data

(60) Provisional application No. 61/110,165, filed on Oct. 31, 2008.

(51) Int. Cl.
| | | |
|---|---|---|
| *C07D 405/12* | (2006.01) | |
| *A61K 9/00* | (2006.01) | |
| *A61K 9/02* | (2006.01) | |
| *A61K 47/48* | (2006.01) | |

(52) U.S. Cl.
CPC ............ *A61K 9/0051* (2013.01); *A61K 9/02* (2013.01); *A61K 47/48038* (2013.01); *C07D 405/12* (2013.01)

(56) References Cited

U.S. PATENT DOCUMENTS

| | | | |
|---|---|---|---|
| 6,040,298 A * | 3/2000 | Adair et al. | 514/50 |
| 8,809,261 B2 * | 8/2014 | Elsohly et al. | 514/1.3 |
| 2008/0112895 A1 * | 5/2008 | Kottayil et al. | 424/46 |
| 2009/0169629 A1 * | 7/2009 | Lambert et al. | 424/489 |
| 2011/0159086 A1 * | 6/2011 | Soler Ranzani et al. | 424/452 |

\* cited by examiner

COMPOSITIONS CONTAINING DELTA-9-THC-AMINO ACID ESTERS AND PROCESS OF PREPARATION

CROSS REFERENCE TO RELATED APPLICATIONS

The present application is a Continuation-in-Part Application of application Ser. No. 13/126,606, filed Jul. 15, 2011, which is a National Stage Application of International Application No. PCT/US09/62998, filed Nov. 2, 2009, which claims priority of U.S. Provisional Application No. 61/110,165, filed Oct. 31, 2008, the entire disclosures of which are incorporated herein in their entireties.

FIELD OF INVENTION

The present invention relates to composition containing delta-9-THC-amino acid esters and their process of preparation.

BACKGROUND OF THE INVENTION

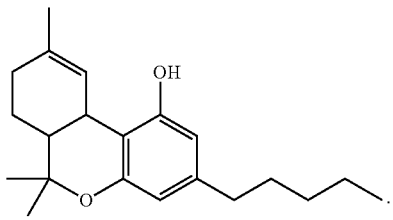

Structure of Δ⁹-Tetrahydrocannabinol (THC)

Δ⁹-Tetrahydrocannabinol (THC, I) is the primary active ingredient of the plant *Cannabis sativa* (marijuana) and is responsible for the majority of the pharmacological effects. People have utilized the plant (that includes numerous cannabinoids) since ancient times for medicinal purposes as well as for its intoxicating properties. While marijuana is primarily known as an abused drug, we believe that there are important pharmacological properties of the active component THC that could be directed to specific therapeutic effects, given the appropriate delivery mechanism. To date, the most promising clinical applications approved by the Food and Drug Administration (FDA) are for the control of nausea and vomiting associated with chemotherapy and for appetite stimulation of AIDS patients suffering from anorexia and wasting syndrome[1, 2].

THC, however, demonstrates other biological activities which lend themselves to possible additional therapeutic applications. These include glaucoma[3], migraine headaches[4, 5] spasticity/epileptic seizures[6, 7], anxiety[8] and chemical dependence withdrawal symptoms. Also, more recently, THC is becoming increasingly recognized as an analgesic[1, 2, 6, 7]. Due to these promising biological activities, THC has potential for multiple medicinal uses.

Challenges in Systemic Delivery of THC:

Parenteral formulations researched include an intramuscular preparation[9] and an intravenous dosage form (neither of which have been approved by FDA). Injectables are inundated with the problems of being invasive and requiring professional assistance, and therefore in many cases preclude self medication. In addition, these parenteral routes are inherently subject to abuse.

Thus, the search for a non-parenteral delivery system for THC continues. The physicochemical characteristics of THC, like many other lipophilic agents, present major challenges to drug delivery scientists. The log P (log octanol/water partition coefficient) value of THC is around 4.0 indicating that it is a highly lipophilic compound. Consequently, THC's solubility in the gastro-intestinal fluids and partitioning from the intestinal membranes into the systemic circulation would be severely limited. Additionally, THC is rapidly metabolized by the hepatic CYP 450 enzymes to the 11-hydroxy metabolite (11-OH-THC), which is responsible for the undesirable side effects of THC[9, 10]. The blood plasma levels desired are in the range of 10 ng/ml—enough to provide a therapeutic effect without the production of a significant "high" (>100 ng/ml)[11, 12]. Poor gastro-intestinal stability of THC further hinders oral absorption. These factors act in conjunction to minimize systemic availability of THC following peroral administration, the most preferred route of administration, and forms the basis of one of the main issues brought into public debate by medicinal marijuana proponents—the fact that the currently available soft gelatin formulation is expensive and lacks consistency in its therapeutic effects and pharmacokinetic profiles. It is significant to note, however, that the only THC dosage form currently approved by FDA is the oral, soft gelatin capsule (Marinol®).

Considering the challenges in intestinal absorption and metabolism, attempts have been made to deliver THC through nasal as well as inhalation routes[13-15]. In a recent phase I pharmacokinetic study[16] performed by GW Pharmaceuticals, UK, *Cannabis*-based extracts were tested by three different routes of administration via; sublingual, buccal and oropharyngeal. The formulation was administered in the form of sublingual drops as well as a pump action sublingual spray (PASS). In this study, it was reported that buccal administration of the PASS test treatment resulted in a later $T_{max}$ but greater $C_{max}$ when compared to the sublingual and oropharyngeal routes. However, AUC was reported to be greatest following the oropharyngeal route. The lower bioavailability (measured in terms of AUC) following buccal administration, as compared to the sublingual and oropharyngeal routes, is most likely related to the difficulty of spraying onto the inside of the cheek and subsequent loss of the spray.

Although promising, the nasal and oropharyngeal routes are burdened with problems. Potential irritation and the irreversible damage to the ciliary action of the nasal cavity from chronic application of nasal dosage forms, and large intra- and inter-subject variability in mucus secretion in the nasal mucosa that could significantly affect drug absorption from this site. Also, the inhalation route of administration possesses high abuse characteristics. In addition, spray formulations of THC have been shown to have a dosage form-related adverse effect of throat irritation[16]. Other non-parenteral routes examined include sublingual[17], rectal[17-20] and vaginal[21].

SUMMARY OF THE INVENTION

This invention comprises compositions containing delta-9-THC-amino acid esters, methods of their preparation and their use in the treatment of different disease conditions.

This invention also describes methods of preparation of delta-9-THC-amino acid esters. The compositions of this invention have not been previously described.

The compounds of this invention represent a class of amino acid esters, one that will improve formulation characteristics and bioavailability of THC.

The amino acid conjugation can yield THC prodrugs that are significantly more hydrophilic and that exhibit greater thermal, chemical and enzymatic stability. These compositions will provide significant treatment options for many disease states known to be ameliorated by THC, including emesis due to chemotherapy, wasting syndrome of HIV patients, multiple sclerosis, glaucoma, spasticity and pain. Administered in the proper formulation, these compositions will decrease the adverse effects of THC therapy (i.e. diminish the levels of the 11-OH-THC metabolite).

Description of the Invention

THC-amino acid esters as prodrugs for THC were prepared in this invention by coupling of THC with allyl protected different amino acids to generate the THC-allyl protected amino acid esters which on deprotection produced THC-amino acid esters. THC (FIG. 1) is used as the starting material for all THC-amino acid esters.

BRIEF DESCRIPTION OF THE FORMULATION INVENTION

The present invention relates to a suppository formulation for effecting bioavailability of $\Delta^9$-THC for the treatment of any disease condition responsive to $\Delta^9$-THC. The formulation comprises a therapeutically effective amount of at least one compound of $\Delta^9$-THC amino ester composition of the formula

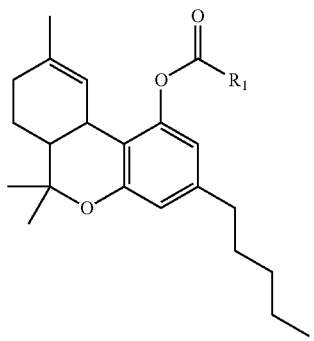

wherein $R_1$ is natural amino acid residue, and salts thereof in an acceptable suppository base. The $\Delta^9$-THC amino ester composition consists essentially of pure $\Delta^9$-THC amino ester.

A further embodiment of the invention comprises a suppository formulation for effecting bioavailability of $\Delta^9$-THC for the treatment of any disease condition responsive to $\Delta^9$-THC which comprises a therapeutically effective amount of at least one compound of a $\Delta^9$-THC amino ester composition of the formula

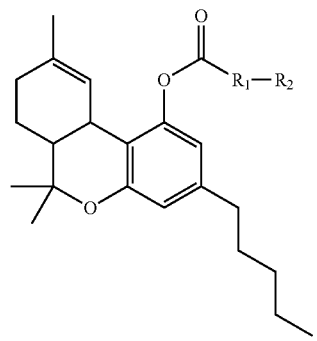

wherein $R_1$ and $R_2$ are residues of natural amino acids, and salts thereof in an acceptable suppository base. The $\Delta^9$-THC amino ester composition consists essentially of a pure $\Delta^9$-THCaminoester.

A still further embodiment of the invention comprises a suppository formulation for effecting bioavailability of $\Delta^9$-THC for the treatment of any disease condition responsive to $\Delta^9$-THC which comprises an effective amount of at least one compound of a $\Delta^9$-THC amino ester composition of the formula

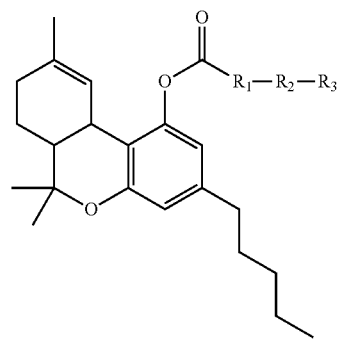

wherein $R_1$, $R_2$ and $R_3$ are residues of natural amino acids, and salts thereof; in an acceptable suppository base and the $\Delta^9$-THC amino ester composition consists essentially of a pure $\Delta^9$-THC amino ester.

The suppository formulations for effecting bioavailability of $\Delta^9$-THC for the treatment of any disease condition responsive to $\Delta^9$-THC can comprise the hemisuccinate or hemigluturate derivative of the $\Delta^9$-THC amino ester compounds of the suppository compositions in the case of the mono, di or tri amino esters of the compositions Furthermore the compounds of the compositions can be the amino esters formed from valine, sarcosine, leucine, glutamine, tryptophan, tyrosine, or alanine and salts thereof.

The present invention can also comprise a suppository formulation for effecting bioavailability of $\Delta^9$-THC for the treatment of any disease condition responsive to $\Delta^9$-THC and can comprise a therapeutically effective amount of at least one compound of $\Delta^9$-THC amino ester composition of the formula

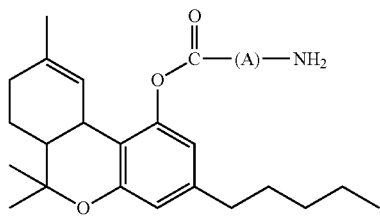

wherein A is a residue of 1, 2 or 3 natural amino acids, and salts thereof; in an acceptable suppository base. The $\Delta^9$-THC amino ester composition consists essentially of a pure $\Delta^9$-THC amino ester.

The suppository formulation can comprise compounds wherein A is the residue of one natural amino acid and salts thereof; wherein A is the residue of two natural amino acids and salts thereof; and wherein A is the residue of three natural amino acids and salts thereof.

The suppository formulations of the invention can comprise the hemisuccinate or hemigluturate derivatives of the $\Delta^9$-THC amino ester compounds included in the formulations. The amino ester of the invention can be formed from amino acids such as for example, valine, sarcosine, leucine, glutamine, tryptophan, tyrosine, or alanine or combinations thereof.

The suppository formulation of of this invention can be suppository formulations in which the suppository base is a hydrophilic base. The suppository formulation can advantageously comprise the suppository formulation base which is a hydrophilic base such as polyethylene glycol 1000.

The present invention also relates to a topical ophthalmic formulation for effecting ocular bioavailability of $\Delta^9$-THC and reducing the intraocular pressure in the treatment of glaucoma. The formulation comprises a therapeutically effective amount of $\Delta^9$-THC amino ester composition of the formula

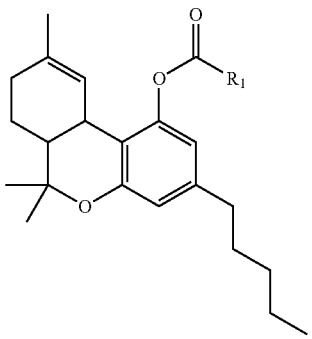

wherein $R_1$ is natural amino acid residue, and salts thereof in acceptable ophthalmic carrier. The $\Delta^9$-THC amino ester composition consists essentially of pure $\Delta^9$-THC amino ester.

A further embodiment of the invention relates to a topical ophthalmic formulation for effecting ocular bioavailability of $\Delta^9$-THC and reducing the intraocular pressure in the treatment of glaucoma. The formulation comprises a therapeutically effective amount of $\Delta^9$-THC amino ester composition of the formula

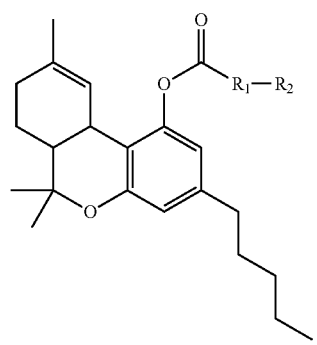

wherein $R_1$ and $R_2$ are residues of natural amino acids, and salts thereof in an acceptable ophthalmic carrier. The $\Delta^9$-THC amino ester composition consists essentially of a pure $\Delta^9$-THCaminoester.

A still further embodiment of the invention comprises a topical ophthalmic formulation for effecting ocular bioavailability of $\Delta^9$-THC and reducing the intraocular pressure in the treatment of glaucoma. The formulation comprises a therapeutically effective amount of $\Delta^9$-THC amino ester composition of the formula wherein $R_1$, $R_2$ and $R_3$ are residues of natural amino acids, and salts thereof; in an acceptable ophthalmic carrier. The $\Delta^9$-THC amino ester composition consists essentially of a pure $\Delta^9$-THC amino ester.

The topical ophthalmic formulation for effecting ocular bioavailability of $\Delta^9$-THC and reducing the intraocular pressure in the treatment of glaucoma can comprise the hemisuccinate or hemigluturate derivative of the $\Delta^9$-THC amino ester compounds of the ophthalmic compositions in the case of the mono, di or tri amino esters of the compositions Furthermore the compounds of the compositions can be the amino esters formed from valine, sarcosine, leucine, glutamine, tryptophan, tyrosine, or alanine and salts thereof.

The present invention can also comprise a topical ophthalmic formulation for effecting ocular bioavailability of $\Delta^9$-THC and reducing the intraocular pressure in the treatment of glaucoma and can comprise a therapeutically effective amount of at least one compound of $\Delta^9$-THC amino ester composition of the formula

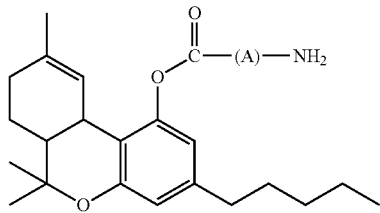

wherein A is a residue of 1, 2 or 3 natural amino acids, and salts thereof; in an acceptable ophthalmic carrier. The $\Delta^9$-THC amino ester composition consists essentially of a pure $\Delta^9$-THC amino ester.

The topical ophthalmic formulation for effecting ocular bioavailability of $\Delta^9$-THC and reducing the intraocular pressure in the treatment of glaucoma can comprise compounds wherein A is the residue of one natural amino acid and salts thereof; wherein A is the residue of two natural amino acids and salts thereof; and wherein A is the residue of three natural amino acids and salts thereof.

The topical ophthalmic formulation for effecting ocular bioavailability of $\Delta^9$-THC and reducing the intraocular pressure in the treatment of glaucoma of the invention can comprise the hemisuccinate or hemigluturate derivatives of the $\Delta^9$-THC amino ester compounds included in the formulations. The amino ester of the invention can be formed from amino acids such as for example, valine, sarcosine, leucine, glutamine, tryptophan, tyrosine, or alanine or combinations thereof.

The topical ophthalmic formulation for effecting ocular bioavailability of $\Delta^9$-THC and reducing the intraocular pressure in the treatment of glaucoma of this invention can be an ophthalmic formulation composed of a micellar solution or is a polymeric ocular film or is an emulsion or lipid nanoparticle formulation.

The present invention relates to a "Transmucosal Delivery Hot Melt Extrusion (HME) Patch" formulation for the treatment of any disease condition responsive to $\Delta^9$-THC. The formulation comprises a therapeutically effective amount of at least one compound of $\Delta^9$-THC amino ester composition of the formula

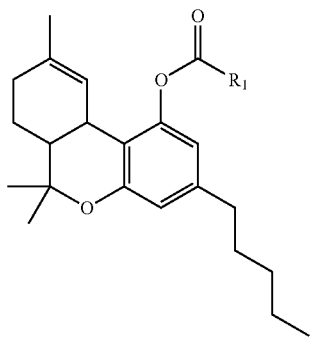

wherein $R_1$ is natural amino acid residue, and salts thereof in in an acceptable HME patch composition. The $\Delta^9$-THC amino ester composition consists essentially of pure $\Delta^9$-THC amino ester.

A further embodiment of the invention relates to a "Transmucosal Delivery Hot Melt Extrusion (HME) Patch" formulation for the treatment of any disease condition responsive to $\Delta^9$-THC. The formulation comprises a therapeutically effective amount of at least one compound of $\Delta^9$-THC amino ester composition of the formula

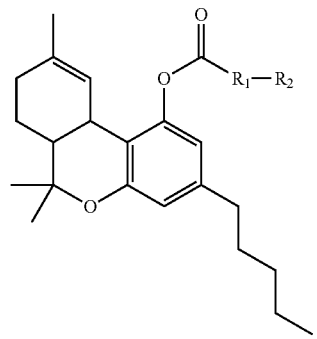

wherein $R_1$ and $R_2$ are residues of natural amino acids, and salts thereof in in an acceptable HME patch composition. The $\Delta^9$-THC amino ester composition consists essentially of a pure $\Delta^9$-THCaminoester.

A still further embodiment of the invention comprises relates to a "Transmucosal Delivery Hot Melt Extrusion (HME) Patch" formulation for the treatment of any disease condition responsive to $\Delta^9$-THC. The formulation comprises a therapeutically effective amount of at least one compound of $\Delta^9$-THC amino ester composition of the formula

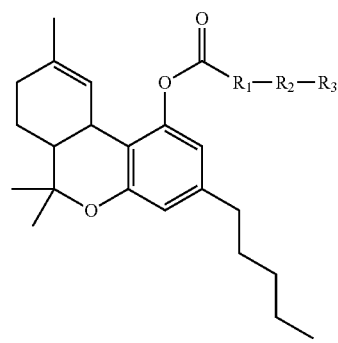

wherein $R_1$, $R_2$ and $R_3$ are residues of natural amino acids, and salts thereof; in in an acceptable HME patch composition and the $\Delta^9$-THC amino ester composition consists essentially of a pure $\Delta^9$-THC amino ester.

The "Transmucosal Delivery Hot Melt Extrusion (HME) Patch" formulation for the treatment of any disease condition responsive to $\Delta^9$-THC can comprise the hemisuccinate or hemigluturate derivative of the $\Delta^9$-THC amino ester compounds in the case of the mono, di or tri amino esters of the compositions.

Furthermore, the compounds of the compositions can be the amino esters formed from valine, sarcosine, leucine, glutamine, tryptophan, tyrosine, or alanine and salts thereof.

The present invention can also comprise a "Transmucosal Delivery Hot Melt Extrusion (HME) Patch" formulation for the treatment of any disease condition responsive to $\Delta^9$-THC and can comprise a therapeutically effective amount of at least one compound of $\Delta^9$-THC amino ester composition of the formula

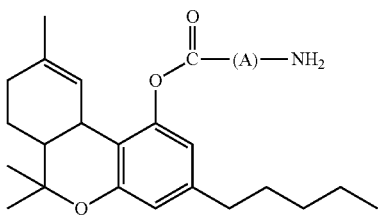

wherein A is a residue of 1, 2 or 3 natural amino acids, and salts thereof; in in an acceptable HME patch composition. The $\Delta^9$-THC amino ester composition consists essentially of a pure $\Delta^9$-THC amino ester.

The "Transmucosal Delivery Hot Melt Extrusion (HME) Patch" formulation for the treatment of any disease condition responsive to $\Delta^9$-THC can comprise compounds wherein A is the residue of one natural amino acid and salts thereof; wherein A is the residue of two natural amino acids and salts thereof; and wherein A is the residue of three natural amino acids and salts thereof.

The "Transmucosal Delivery Hot Melt Extrusion (HME) Patch" formulation for the treatment of any disease condition responsive to $\Delta^9$-THC of the invention can comprise the hemisuccinate or hemigluturate derivatives of the $\Delta^9$-THC amino ester compounds included in the formulations. The amino ester of the invention can be formed from amino acids such as for example, valine, sarcosine, leucine, glutamine, tryptophan, tyrosine, or alanine or combinations thereof.

The "Transmucosal Delivery Hot Melt Extrusion (HME) Patch" formulation for the treatment of any disease condition responsive to $\Delta^9$-THC of this invention can be "Transmucosal Delivery Hot Melt Extrusion (HME) Patch" formulation for the treatment of any disease condition responsive to $\Delta^9$-THC in which the HME patch comprises polyethylene oxide N10 (159.4 mg), 6 mg Brij 98, 4 mg sodium deoxycholate, 2 mg citric acid and 10 mg Vitamin E Succinate.

Delta-9-tetrahydrocannabinol ($\Delta^9$-THC) is the active ingredient of the plant *Cannabis sativa* (marijuana) which is responsible for the majority of the pharmacological effects of the plant. Therapeutic activities associated with marijuana use or administration of $\Delta^9$-THC include, but are not limited to, antiemetic activity as disclosed in Sallan, S. E.; Zinberg, N. E.; and Frei, E., III. Antiemetic effect of delta-9-tetrahydrocannabinol in patients receiving cancer chemotherapy. N. Engl. J. Med., 293:795-797, 1975; Sallan, S. E.; Cronin, C.; Zelen, M.; and Zinberg, N. E. Antiemetics in patients receiving chemotherapy for cancer. N. Engl. J. Med., 302: 135-138, 1980; Ungerleider, J. T.; Fairbanks, L. A.; and Andrysiak, T. THC or compazine for cancer chemotherapy patient—the USLA Study, Part II: Patient drug preference. Am. J. Clin. Oncol., 8:142-147, 1985; and Regelson, W.; Butler, J. R.; Schultz, J.; Kirk, T.; Peek, L.: Green, M. L.; and Zalis, M. O. The Pharmacology of Marihuana, Vol. 2, Eds. M. C. Braude and S. Szara, Raven Press, N.Y., 1976, pp. 763-776, Analgesic activity is disclosed in Maurer, M.; Henn, V.; Dirtrich, A.; and Hofmann, A. Delta-9-tetrahydrocannabinol shows antispastic and analgesic effects in a single case double-blind trial. Eur. Arch. Psychiatry Clin. Neurosci., 240(1):1-4, 1990; Noyes, R.; Brunk, S. F; Avery, D. H.; and Canter, A. Psychologic effects of oral delta-9-tetrahydrocannabinol in advanced cancer patients. Compr. Psychiat., 17(5):641-646, 1976; and Regelson et al. ibid.

Anti-spasticity is discussed in Maurer et al. ibid. Appetite stimulation is noted by Maurer et al. and Noyes et al. ibid and Gagnon, M. A. and Eli, R. Les effets de la marijuana et de la d-amphetamine sur l'appetit, la consommation alimentire et quelques variables cardio-respiratoires chez l'homme (Effects of marihuana and of d-amphetamine on appetite, food intake, and some cardio-respiratory variables in man). Union Med. Can., 104(6):914-921, 1975; Foltin, R. W.; and Fischmann, M. W. Behavioral analysis of marijuana effects on food intake in humans. Pharmacol. Biochem. Behav., 30(2):551, 1988; Foltin, R. W.; Brady, J. V.; and Fischman, M. W. Behavioral analysis of marijuana effects on food intake in humans. Pharmacol. Biochem. Behav., 25(3), 557-582, 1986; Bruera, E. Current pharmacological management of anorexia in cancer patients. Oncology, Williston Park, 6(1), 125-130, 1992).

Antidepressant activity is discussed in Regelson et al and Maurer et al, ibid. Treatment and prevention of migraine headache is discussed by El-Mallakh, R. S. Marihuana and migraine. Headache, 27(8):442-443, 1987; and Volfe, Z.; Dvilansky, A.; and Nathan, I. Cannabinoids block release of serotonin from platelets induced by plasma from migraine patients. Int. J. Clin. Pharmacol. Res., 5(4):243-246, 1985.

Anti-anxiety is disclosed by McLendon, D. M.; Harris, R. T.; and Maule, W. F. Suppression of the cardiac conditioned response by delta-9-tetrahydrocannabinol: A comparison with other drugs. Psychopharmacology, 50(2):159-163, 1976; and Musty, R. E. Possible anxiolytic effects of cannabidiol. The Cannabinoids: Chemical, Pharmacologic, and Therapeutic aspects, Eds. S. Agurell, W. L. Dewey, and R. E. Willette, Academic Press, Orlando, Fla., 1984).

Treatment of glaucoma is the subject of Hepler, R. S.; Frank, I. M.; and Petrus R. Occular effects of marihuana smoking. In: The Pharmacology of Marihuana, Eds. M. C. Braude and S. Szara, Raven Press, New York, 1976, pp. 815-824; ElSolhy, M. A.; Harland, E.; and Waller, C. W. Cannabinoids in Glaucoma II: The effect of different cannabinoids on the intraocular pressure of the rabbit. Curr. Eye Res., 3(6):841-850, 1984).

Improvement of night vision is taught by Reese, K. M. *Cannabis* seems to improve night vision of fisherman. Chem. Eng. News. 69(31):44, 1991; and West, M. E. *Cannabis* and night vision. Nature. 351(6329):703-704, 1991).

Suppository bases can be classified according to their physical characteristics into two main categories and a third miscellaneous group: (a) fatty or oleaginous bases, (b) water-soluble or water-miscible bases, and (c) miscellaneous bases, generally combinations of lipophilic and hydrophilic substances.

Among the fatty or oleaginous materials used in suppository bases are cocoa butter and many hydrogenated fatty acids of vegetable oils, such as palm kernel oil and cottonseed oil. Also, fat-based compounds containing compounds of glycerin with the higher-molecular-weight fatty acids, such as palmitic and stearic acids, may be found in fatty bases. Such compounds, such as glyceryl monostearate and glyceryl monopalmitate, are examples of this type of agent. The bases in many commercial products employ varied combinations of these types of materials to achieve the desired hardness under conditions of shipment and storage and the desired quality of submitting to the temperature of the body to release their medicaments. Some bases are prepared with the fatty materials emulsified or with an emulsifying agent present to prompt emulsification when the suppository makes contact with the aqueous body fluids. These types of bases are arbitrarily placed in the third, or miscellaneous, group of bases.

Cocoa Butter, NF, is defined as the fat obtained from the roasted seed of *Theobroma cacao*. At room temperature, it is a yellowish-white solid having a faint, agreeable chocolate-like odor. Chemically, it is a triglyceride (combination of glycerin and one or different fatty acids) primarily of oleopalmitostearin and oleodistearin.

Other bases in this category include commercial products such as Fattibase (triglycerides from palm, palm kernel, and coconut oils with self-emulsifying glyceryl monostearate and polyoxyl stearate), the Wecobee bases (triglycerides derived from coconut oil) and Witepsol bases (triglycerides of saturated fatty acids C12-C18 with varied portions of the corresponding partial glycerides).

The main members of water-soluble and water-miscible suppository bases are glycerinated gelatin and polyethylene glycols. Glycerinated gelatin suppositories may be prepared by dissolving granular gelatin (20%) in glycerin (70%) and adding water or a solution or suspension of the medication (10%).

Polyethylene glycols are polymers of ethylene oxide and water prepared to various chain lengths, molecular weights, and physical states. They are available in a number of molecular weight ranges, the most commonly used being polyethylene glycol 300, 400, 600, 1,000, 1,500, 1,540, 3,350, 4,000, 6,000, and 8,000. The numeric designations refer to the average molecular weight of each of the polymers. Polyethylene glycols having average molecular weights of 300, 400, and 600 are clear, colorless liquids. Those having average molecular weights of greater than 1,000 are waxlike white solids whose hardness increases with an increase in the molecular weight. Melting ranges for the polyethylene glycols follow:

| | |
|---|---|
| 300 | −15° C.-18° C. |
| 400 | 4° C.-8° C. |
| 600 | 20° C.-25° C. |
| 1000 | 37° C.-40° C. |
| 1450 | 43° C.-46° C. |
| 3350 | 54° C.-58° C. |
| 4600 | 57° C.-61° C. |
| 6000 | 56° C.-63° C. |
| 8000 | 60° C.-63° C. |

Various combinations of these polyethylene glycols may be combined by fusion, using two or more of the various types to achieve a suppository base of the desired consistency and characteristics.

In the miscellaneous group of suppository bases are mixtures of oleaginous and water-soluble or water-miscible materials. These materials may be chemical or physical mixtures. Some are preformed emulsions, generally of the water-in-oil type, or they may be capable of dispersing in aqueous fluids. One of these substances is polyoxyl 40 stearate, a surface-active agent that is employed in a number of commercial suppository bases. Polyoxyl 40 stearate is a mixture of the monostearate and distearate esters of mixed polyoxyethylene diols and the free glycols, the average polymer length being equivalent to about 40 oxyethylene units. The substance is a white to light tan waxy solid that is water soluble. Its melting point is generally 39° C. to 45° C. (102° F. to 113° F.). Other surface-active agents useful in the preparation of suppository bases also fall into this broad grouping. Mixtures of many fatty bases (including cocoa butter) with emulsifying agents capable of forming water-in-oil emulsions have been prepared. These bases hold water or aqueous solutions and are said to be hydrophilic.

The preferred suppository bases in the present invention are water soluble or water miscible bases.

The transmucosal device film or films (in the case of co-extrusion or layering) generally comprises at least one water-soluble, water-swellable or water-insoluble thermoplastic polymer. The thermoplastic polymer used to prepare the HME film may include, but is not limited to polytheylene oxide (PolyOx®), polyvinylpyrrolidone (Kollidon®), hydroxypropyl cellulose (Klucel®), ethyl cellulose, methylcellulose, alkylcelluloses, veegums clays, alginates, PVP, alginic acid, carboxymethylcellulose calcium, microcrystalline cellulose (e.g., Avicel™), polacrillin potassium (e.g., Amberlite™), sodium alginate, corn starch, potato starch, pregelatinized starch, modified starch, cellulosic agents, montmorrilonite clays (e.g., bentonite), gums, agar, locust bean gum, gum karaya, pecitin, tragacanth, and other matrix formers known to those skilled in the art.

This matrix may optionally contain a bioadhesive (such as a carbopol, polycarbophil, chitosan or others known to those skilled in the art—to further enhance the bioadhesivity of the cannabinoid itself) or a bioadhesive layer may be laminated onto the matrix film or patch containing the cannabinoid. In addition, an impermeable backing layer may be incorporated to insure unidirectional flow of the drug through the patient's mucosa. In some cases, a rate controlling film or membrane may also be laminated or sprayed onto the cannabinoid-containing matrix to further control the rate of release of the actives.

The transmucosal preparation will preferably contain a 'penetration enhancer' (which may also be referred to as an absorption enhancer or permeability enhancer). These penetration enhancers may include bile salts, such as sodium deoxycholate, sodium glycodeoxycholate, sodium taurocholate and sodium glycocholate, surfactants such as sodium lauryl sulfate, polysorbate 80, laureth-9, benzalkonium chloride, cetylpyridinium chloride and polyoxyethylene monoalkyl ethers such as the BRIJ® and MYRJ® series. Additional penetration enhancers for inclusion in the embodiment include benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, cyclodextrins, the sulfoxides, such as dimethyl sulfoxide and dodecyl methyl sulfoxide, the terpenes, such as menthol, thymol and limonene, urea, chitosan and other natural and synthetic polymers.

The hot-melt extruded or hot-melt molded matrix may also comprise as bioadhesives such as water-soluble or water-swellable polymers derived from acrylic acid or a pharmaceutically acceptable salt thereof, such as the polyacrylic acid polymers, including carbomers, polycarbophils and/or water-soluble salts of a co-polymer of methyl vinyl ether and maleic acid or anhydride (Gantrez MS-955).

The transmucosal preparation can also comprise one or more pH-adjusting agents to improve stability and solubility. Also the pH modifying agents can control cannabinoid release and enhance bioadhesion. A pH-adjusting agent can include, by way of example and without limitation, an organic acid or base, an alpha-hydroxy acid, or a beta-hydroxy acid. Suitable agents include tartaric acid, citric acid, fumaric acid, succinic acid and others known to those of ordinary skill in the art.

The transmucosal preparation can also comprise one or more cross-linking agents to reduce matrix erosion time, control release of the cannabinoid or enhance bioadhesion. A cross-linking agent can include, by way of example and without limitation, an organic acid, an alpha-hydroxy acid, or a beta-hemolytic-hydroxy acid. Suitable cross-linking agents include tartaric acid, citric acid, fumaric acid, succinic acid and others known to those of ordinary skill in the art.

The transmucosal preparation may also contain other components that modify the extrusion, molding or casting characteristics or physical properties of the matrix. Such other components are well known to those of ordinary skill in the pharmaceutical sciences and include, for example, polyethylene, xylitol, sucrose, surface-active agents, others known to those skilled in the art, and combinations thereof.

The transmucosal preparation of the present invention can also include super-disintegrants or absorbents. Examples of such are sodium starch glycolate (Explotab™, Primojel™) and croscarmellose sodium (Ac-Di-Sol®). Other suitable absorbents include cross-linked PVP (Polyplasdone™ XL 10), clays, alginates, corn starch, potato starch, pregelatinized starch, modified starch, cellulosic agents, montmorrilonite clays (bentonite), gums, agar, locust bean gum, gum karaya, pectin, tragacanth, and other disintegrants known to those of ordinary skill in the art.

The transmucosal preparation of the invention can include a chelating agent. Suitable chelating agents include EDTA, polycarboxylic acids, polyamines, derivatives thereof, and others known to those of ordinary skill in the art.

The transmucosal preparation of the invention can include a surfactant. Suitable surfactants include sucrose stearate, Vitamin E derivatives, sodium lauryl sulfate, dioctyl sodium sulfosuccinate, and others known to those of ordinary skill in the art.

The transmucosal preparation of the invention can include a preservative. Preservatives include compounds used to prevent the growth of microorganisms. Suitable preservatives include, by way of example and without limitation, benzalkonium chloride, propyl paraben, methyl paraben, benzyl alcohol, cetylpridinium chloride, chlorobutanol, sorbic acid, phenol, phenylethyl alcohol, phenylmercuric nitrate and thimerosal and others known to those of ordinary skill in the art.

As used herein, the term "flavorant", "flavor" or "fragrance" is intended to mean a compound used to impart a pleasant flavor and often odor to a pharmaceutical preparation, in addition to the natural flavorants, many synthetic flavorants are also used. Such compounds include, by way of example and without limitation, anise oil, cinnamon oil, cocoa, menthol, orange oil, peppermint oil and vanillin and others known to those of ordinary skill in the art. Flavors incorporated in the composition may be chosen from synthetic flavor oils and flavoring aromatics and/or natural oils, extract from plants, leaves, flowers, fruits and so forth and combinations thereof. These may include oil of wintergreen, clove oil, bay oil, anise oil, eucalyptus, thyme oil, cedar leaf oil, oil of nutmeg, oil of sage, oil of bitter almonds and cassia oil. Also useful as flavors are vanilla, citrus oils, including lemon, orange, lime and grapefruit, and fruit essences, including grape, apple, pear, peach, strawberry, raspberry, cherry, plum, apricot, and so forth. Flavors that have been found to be particularly useful include commercially available orange, grape, cherry, and bubble gum flavors and mixtures thereof. The amount of flavoring may depend on a number of factors, including the organoleptic effect desired.

As used herein, the term "colorant" is intended to mean a compound used to impart color to solid pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide red. Other suitable colorants include titanium dioxide and natural coloring agents such as grape extract, beet red powder, carmine, turmeric, paprika, and others known to those of ordinary skill in the art.

The transmucosal preparation of the invention can include an antioxidant to prevent the deterioration of preparations by oxidation. These compounds include, by way of example and without limitation, ascorbic acid, ascorbyl palmitate, butylated hydroxyanisole (BHA), butylated hydroxytoluene (BHT), hypophophorous acid, monothioglycerol, sodium ascorbate, sodium formaldehyde sulfoxylate and sodium metabisulfate and others known to those of ordinary skill in the art. Other suitable antioxidants include, for example, vitamin C, sodium bisulfite, vitamin E and its derivatives, propyl gallate, a sulfite derivative, and others known to those of ordinary skill in the art.

The transmucosal preparation of the invention may contain a release rate modifier. Suitable release rate modifiers include hydroxypropylcellulose (HPC), poly(ethylene oxide) (PEO), hydroxypropyl methlcellulose (HPMC), ethylcellulose, cellulosic polymers, acrylic polymers, fat, waxes, lipid, or a combination thereof, in some embodiments, the release rate modifier is polycarbophil, carbomer or a polysaccharide. The ingredients and chemicals used for the production of the transmucosal preparation used in this invention are of acceptable quality, preferably pharmaceutically acceptable quality. The cannabinoid-containing transmucosal preparation is homogenous and pharmaceutically acceptable.

The transmucosal preparation of the invention can include stabilizers to protect against hydrolysis. Such stabilizers may include cyclodextrins, chelating agents and surfactants.

The topical ophthalmic formulation can be solutions, emulsions, lipid nanoparticulates or matrix films. Other formulations known to one skilled in the art may also be used. The lipid nanoparticulates, emulsions and matrix films are the most preferred formulations.

Solutions:

The solution formulations typically will require solubilizers in view of the low solubility of the THC prodrugs. Examples of solubilizers that can be used in ophthalmic formulations include surfactants which form micellar solutions (since the active ingredient is entrapped in micelles) and complex forming agents or combinations thereof. Commonly used surfactants in ophthalmic formulations include polyoxyethylene sorbates (e.g. Tween® 20 and Tween® 80), polyoxyl hydrogenated castor oils (e.g. Cremphor® EL and Cremophor® RH 40), Tyloxapol®, polyoxyethyelene ethers (Brij® series) and alkoxylated fatty acid esters (Myrj® series), sorbitan esters (Span® series) and others know to a person skilled in the art. Cyclodextrins, such as hydroxypropyl betacyclodextrin and randomlymethylated beta cyclodextrins, are commonly used to enhance solubility through inclusion complex formation. The solubilizers may be used alone or in combination.

Emulsions:

An emulsion is a system consisting of two immiscible liquid phases (oil and water), one of which is dispersed throughout the other as fine droplets, the system being stabilized by a third component, the emulsifying agent. Emulsions are inherently unstable, and emulsifiers are essential for both their initial formation and long-term stability. Emulsions may be oil in water (oil phase dispersed in the aqueous phase) or water in oil (water phase dispersed in the oil phase) emulsions. A variety of other systems such as oil in water in oil emulsions and water in oil in water emulsions are also known in the art. The oil phase may consist of oils such as soyabean oil, castor oil, sesame oil and olive oil. Several emulsion stabilizers or emulsifying agents are known in the art and include surfactants and phospholipids. Examples of surfactant emulsifiers include polyoxyethylene sorbates (e.g. Tween® 20 and Tween® 80), polyoxyl hydrogenated castor oils (e.g. Cremphor® EL and Cremophor® RH 40), Tyloxapol®, polyoxyethyelene ethers (Brij® series) and alkoxylated fatty acid esters (Myrj® series), sorbitan esters (Span® series) and others know to a person skilled in the art. Examples of phospholipids that may be used as emulsion stabilizers include phospholipids (e.g. phosphatidylcholine, phosphatidylinositol, phosphatidylglycerol).

Lipid Nanoparticles:

Colloidal dispersions of solid lipid nanoparticles (SLNs) or nanostructured lipid carriers (NLCs) containing the therapeutic agent may also be used. In these systems, the drug is loaded in the lipid phase, which is then dispersed in the aqueous phase. In the design of SLNs, only lipids that are solid at room temperature are used whereas with NLCs a combination of solid (e.g. Compritol®, Precirol®) and liquid lipids (e.g. Miglyol®) are used. Additionally, stabilizers such as surfactants and other components such as glycerine and propylene glycol may also be used alone and in combination thereof.

Matrix Films:

Matrix films prepared using melt-extrusion or melt-cast technology can also be used. The films comprise a thermoplastic polymer as the carrier of the active ingredient. The thermoplastic polymer used may include, but is not limited to polytheylene oxide (PolyOx®), polyvinylpyrrolidone (Kollidon®), hydroxypropyl cellulose (Klucel®), ethyl cellulose, methylcellulose, alkylcelluloses, veegums clays, alginates, PVP, alginic acid, carboxymethylcellulose calcium, microcrystalline cellulose (e.g., Avicel™), polacrillin potassium (e.g., Amberlite™), sodium alginate, corn starch, potato starch, pregelatinized starch, modified starch, cellulosic agents, montmorrilonite clays (e.g., bentonite), gums, agar, locust bean gum, gum karaya, pecitin, tragacanth, and other matrix formers known to those skilled in the art. The matrix film may also comprise of bioadhesives such as water-soluble or water-swellable polymers derived from acrylic acid or a pharmaceutically acceptable salt thereof, such as the polyacrylic acid polymers, including carbomers, polycarbophils and/or water-soluble salts of a co-polymer of methyl vinyl ether and maleic acid or anhydride (Gantrez MS-955).

The topical ophthalmic compositions may include additional or alternative polymeric ingredients and/or viscosity agents to increase stability and/or retention on the ocular surface. Examples include carboxymethylcellulose, hydroxypropylmethyl cellulose, hydroxyethyl cellulose, carboxyvinyl polymer, xanthan gum, hyaluronic acid, any combinations thereof or the like.

The topical ophthalmic compositions may include a preservative. Potential preservatives include quaternium ammonium compounds such as benzalkonium chloride, hydrogen peroxide and other ophthalmic preservatives/preservative systems known in the art.

Other additives such as buffers and tonicity adjusting agents may also be included in the topical ophthalmic combinations. Examples of buffering agents include citrate, borate and acetate buffers. Tonicity adjusting agents may include for example sodium chloride and potassium chloride. Additionally stabilizers (e.g. antioxidants and chelating agents) and penetration enhancers e.g. benzalkonium chloride, saponins, fatty acids, polyoxyethylene fatty ethers, alkyl esters of fatty acids, pyrrolidones, polyvinylpyrrolidone, pyruvic acids, pyroglutamic acids and their mixtures, among others, may also be included.

THC Prodrugs

Figure 1:
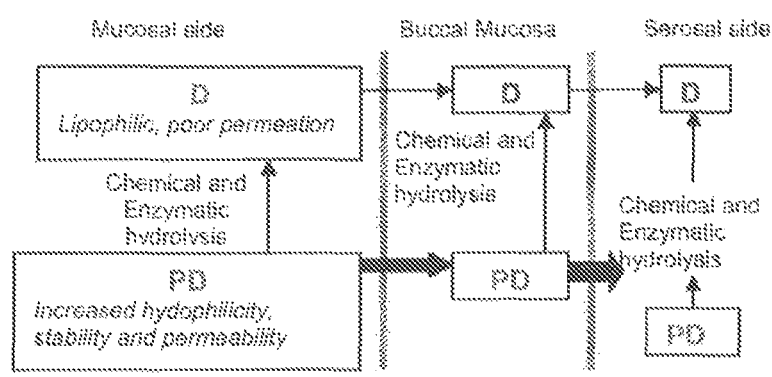
FIG. 1: Schematic representation of the utility of the prodrug/TMP system concept. Prodrug (PD) derivatization of the parent drug THC (D), in combination with the TMP system improves overall permeability. Transbuccal permeability and bioreversion are illustrated by arrows. Line thickness represents the extent and higher or lower rates of permeability.

Chemical modification of a therapeutic agent by way of prodrug design has become an important drug delivery tool[22-24]. This is one of the most widely accepted and successful strategies for modifying physicochemical characteristics, aqueous solubility, chemical and enzymatic stability and mucosal permeability of drug candidates through linkage of appropriate promoieties. A significant positive aspect of the prodrug approach is that it does not induce any change in the membrane structure, fluidity or characteristics. The prodrugs are cleaved in vivo to generate the active drug and the harmless pro-moiety, which is eliminated from the body (FIG. 1).

Amino Acid Prodrugs:

In the past decade amino acids have taken center stage as promoieties for transporter targeted prodrug derivatization of hydrophilic drug molecules[25-31]. Some studies exploiting this mechanism for circumvention of efflux proteins have also been published[32-35]. A few studies exploring the use of single amino acid based prodrug derivatization to enhance hydrophilicity of lipophilic molecules and improve oral absorption have also been reported[28, 36-46]. However, to date, transbuccal delivery of mono-, di- or tri-amino acid conjugated prodrugs of lipophilic compounds has not been investigated. Indeed, a major gap in the understanding of the structural and physicochemical characteristics of any molecule necessary for transbuccal penetration exists. This route of administration holds tremendous untapped potential for the delivery of many therapeutic agents with limited permeability and metabolic stability. Compounds whose systemic bioavailability is limited by hepatic metabolism, as in the case of THC, will necessitate preparation of more permeable prodrugs, such as the mono-, di- and tri-amino acid esters to be formulated in non-oral formulations such as the Transmucosal Matrix Patch (TMP) system with a multitude of advantages. However, the above-cited prodrugs could also be incorporated into an oral delivery system and other compositions using processing techniques, including, but not limited to, hot-melt extrusion to enhance bioavailability. The highlight of this invention is the ability, for the first time, to prepare amino acid esters of THC, without affecting the basic structure of THC.

Increasing the bioavailability of THC, through the use of the amino acid esters prodrugs and incorporating these prodrugs in a formulation such as the Transmucosal Matrix Patch (TMP), or a more efficient oral delivery system, could have a significant influence on many chronically ill patients, such as those infected with the HIV virus, those undergoing chemotherapy, as well as other conditions known to be ameliorated by THC, such as pain, spasticity and multiple sclerosis.

The pharmacologically acceptable compounds of the present invention can be used, for example, for the manufacture of pharmaceutical compositions useful in treatment of chronic states treatable with THC and which contain an effective amount of the active substance together or in admixture with inorganic or organic, solid or liquid, pharmaceutically acceptable carriers.

The pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. A preferred method of use for the present compositions is by transmucosal patch. The dosage of the active substance depends on the species of warm-blooded animal and on the age and individual condition the illness to be treated and also on the mode of administration.

THC-Amino Acid Prodrugs:

Computational analysis of the amino acid based THC prodrugs: Based on the previous findings, computational analysis, using Molecular modeling Pro® software, was utilized to predict the physicochemical properties of various promoiety candidates.

Computational analysis was subsequently performed with some of the amino acids classified under the hydrophobic amino acid group (e.g. alanine, leucine, valine), as well as with the hydrophilic amino acids (e.g. glycine, serine, sarcosine, aspartic acid, tyrosine and glutamine), and their combinations. These results are depicted in Table 1.

TABLE 1

Computed physicochemical properties of select amino acid ester prodrugs of THC. Molecular modeling Pro Software was used for this purpose.

| Sr. No. | Compound | Molecular weight | Molecular formula | mLogP | % hydrophilic surface area | Polar surface area |
|---|---|---|---|---|---|---|
| 1 | THC | 314.46 | $C_{21}H_{30}O_2$ | 3.963 | 5.742 | 29.46 |
| 2 | THC-Ala | 385.54 | $C_{24}H_{35}NO_3$ | 2.438 | 13.163 | 64.71 |
| 3 | THC-Leu | 427.61 | $C_{27}H_{41}NO_3$ | 3.051 | 11.465 | 64.71 |
| 4 | THC-Val | 413.59 | $C_{26}H_{39}NO_3$ | 2.850 | 11.889 | 64.71 |
| 5 | THC-Gly | 371.25 | $C_{23}H_{33}NO_3$ | 2.227 | 16.702 | 64.71 |
| 6 | THC-Ser | 401.54 | $C_{24}H_{35}NO_4$ | 3.183 | 22.742 | 84.94 |
| 7 | THC-Sar | 385.26 | $C_{24}H_{35}NO_3$ | 2.438 | 21.070 | 50.72 |
| 8 | THC-Asp | 429.55 | $C_{25}H_{35}NO_5$ | 3.286 | 21.844 | 105.17 |
| 9 | THC-Tyr | 477.63 | $C_{30}H_{39}NO_4$ | 2.683 | 16.064 | 84.94 |
| 10 | THC-Tyr-Gln | 605.8 | $C_{35}H_{47}N_3O_6$ | 4.27 | 28.687 | 163.45 |
| 11 | THC-Tyr-(Gln)$_2$ | 733.9 | $C_{40}H_{55}N_5O_8$ | 3.32 | 35.529 | 244.95 |
| 12 | THC-Gln | 442.28 | $C_{26}H_{38}N_2O_4$ | 2.36 | 22.833 | 110.96 |
| 13 | THC-Gln-Val | 541.35 | $C_{31}H_{47}N_3O_5$ | 4.95 | 25.434 | 143.22 |
| 14 | THC-Gln-Val-Val | 640.42 | $C_{36}H_{56}N_4O_6$ | 5.98 | 27.886 | 175.48 |
| 15 | THC-Val-Gly | 470.64 | $C_{28}H_{42}N_2O_4$ | 4.296 | 20.319 | 96.97 |
| 16 | THC-Val-Gly-Gly | 527.70 | $C_{30}H_{45}N_3O_5$ | 5.782 | 27.276 | 129.23 |

The results predict a significant decrease in the log P values and increase in hydrophilicity with both hydrophilic and hydrophobic amino acid prodrugs evaluated. The polar surface area and the % hydrophilic surface area are also significantly improved. Additionally the di- and tri-amino acid (peptide) linkages will allow significant modulation of the physicochemical properties. Thus depending on the type of amino acid selected and the number of amino acids linked to THC, a wide range of hydrophilicities can be generated and permeabilities determined. Thus, the correlation of log P and permeability can be determined.

THC-Amino Acid Esters Synthesis:

Several procedures were attempted for the preparation of the $\Delta^9$-THC amino acid derivatives using the t-boc and F-moc protected amino acids. While the formation of the esters with the protected amino groups was not problematic for all of the amino acid derivatives attempted, deprotection of the t-boc or the F-moc groups under various deprotection conditions always resulted in conversion of the $\Delta^9$-THC (at least in part) to $\Delta^8$-THC, in case of the t-boc, or reversion to $\Delta^9$-THC in the case of the F-moc. In this invention, we have developed allyl protected amino acids prepared in house (scheme I) to overcome the problems associated with the commonly available protected amino acids. This approach proved to be successful and promises viability in the preparation of any amino acid derivative or small chain peptide derivatives of $\Delta^9$-THC without any effect on the rest of the structure. The di-amino acid derivative could be converted to the tri-amino acid derivative following the same procedure as for the conversion of the mono- to the di-derivative.

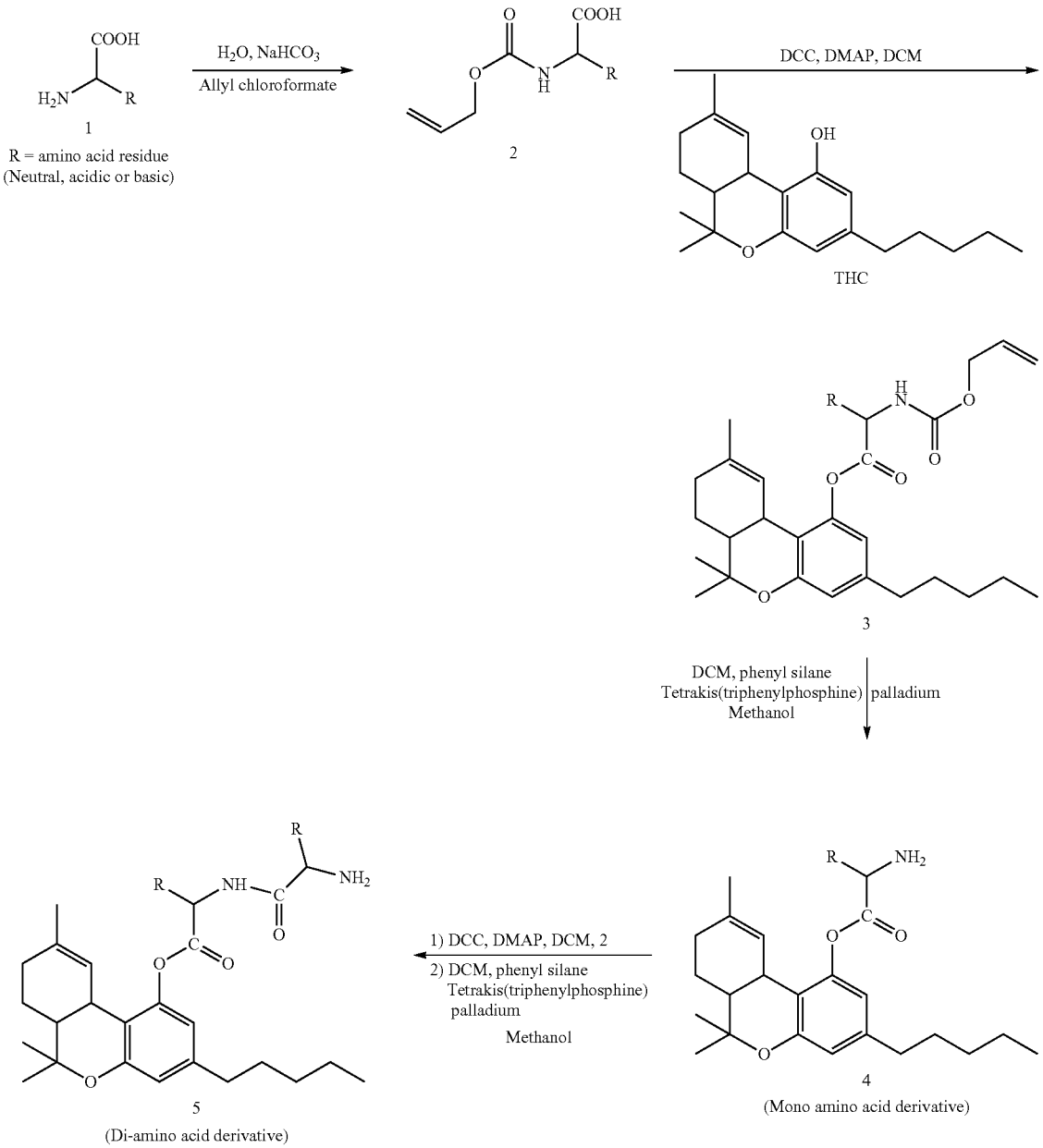

Scheme I.
General scheme for the preparation of mono, di and tri-amino acid THC derivatives.

Examples of amino acid esters prepared according to scheme I, are: $\Delta^9$-THC-valinate (6), THC-sarcosinate (7), THC-leucinate (8), THC-glutaminate (9) THC-tryptophinate (10), THC-tyrosinate (11) and THC-B-alaninate (12) were prepared. The compounds THC-4-(4-amino-phenyl)butyrate) (13), and THC-4-(4-amino-phenyl)butyrate) hemisuccinate (14) and THC-valinate-hemisuccinate (15) were prepared using scheme II.

Their structures were confirmed by mass (LC/MS and HREIMS) and spectroscopic analysis ($^1$H-NMR and $^{13}$C-NMR).

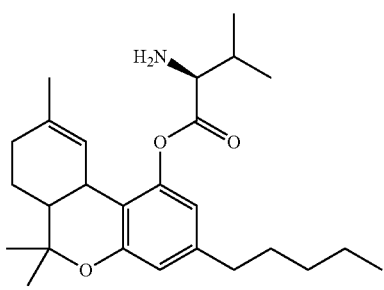

Chemical Formula: $C_{26}H_{39}NO_3$
Molecular Weight: 413.5928
THC-valinate
(6)

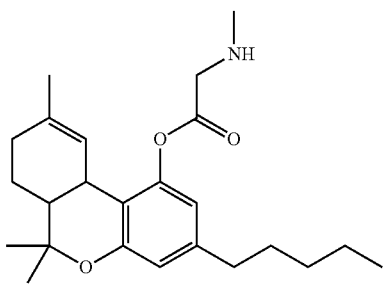

Chemical Formula: $C_{24}H_{35}NO_3$
Molecular Weight: 385.5396
THC-sarcosinate
(7)

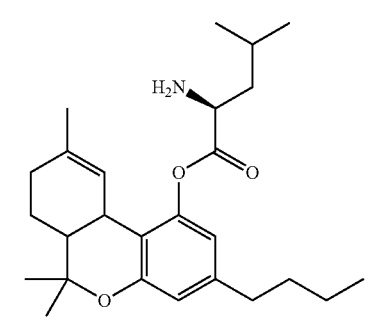

Chemical Formula: $C_{26}H_{39}NO_3$
Molecular Weight: 413.5928
THC-leucinate
(8)

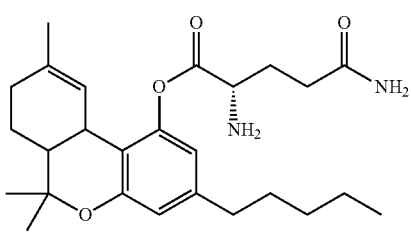

Chemical Formula: $C_{26}H_{38}N_2O_4$
Molecular Weight: 442.5909
THC-glutaminate
(9)

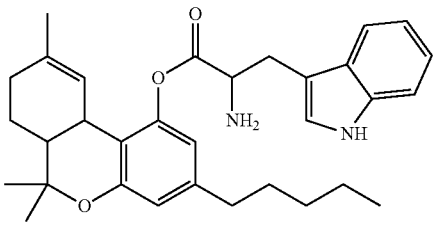

Chemical Formula: $C_{32}H_{40}N_2O_3$
Molecular Weight: 500.6716
THC-tryptophanate
(10)

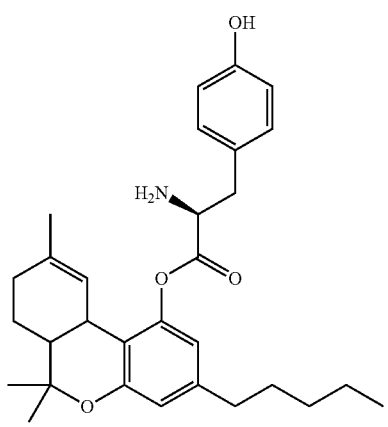

Chemical Formula: $C_{30}H_{39}NO_4$
Molecular Weight: 477.6350
THC-tyrosinate
(11)

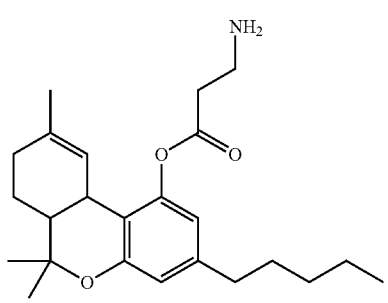

Chemical Formula: $C_{24}H_{35}NO_3$
Molecular Weight: 385.5396
THC-B-alaninate
(12)

-continued

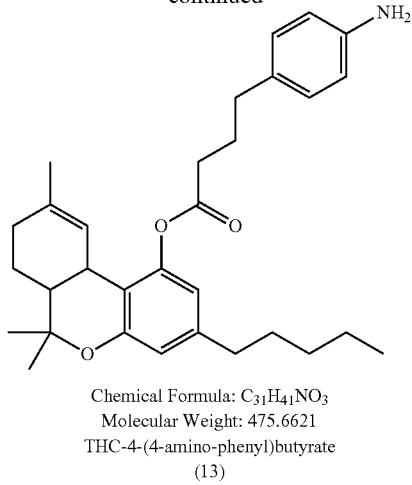

Chemical Formula: $C_{31}H_{41}NO_3$
Molecular Weight: 475.6621
THC-4-(4-amino-phenyl)butyrate
(13)

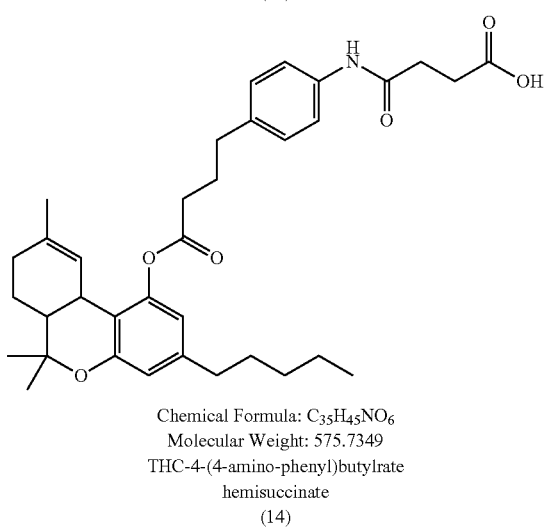

Chemical Formula: $C_{35}H_{45}NO_6$
Molecular Weight: 575.7349
THC-4-(4-amino-phenyl)butylrate hemisuccinate
(14)

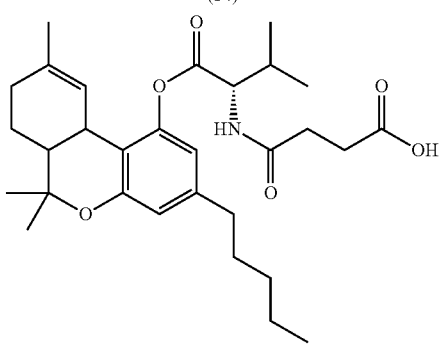

Chemical Formula: $C_{30}H_{43}NO_6$
Molecular Weight: 513.6655
THC-valinate-hemisuccinate
(15)

EXAMPLES (COMPOUNDS 6-15)

Example 1: Preparation of $\Delta^9$-THC-valinate (6)

Following the general procedure outlined in Scheme I, where compound 1 is valine, $\Delta^9$-THC-valinate 6 was synthesized to test the validity of the synthetic protocol. Valine (5 g) was dissolved in 34 mL of distilled water and 5.8 gram of sodium carbonate was added in several portions. Allyl chloroformate (10 mL) was added at once after the bubbling stopped. The solution was stirred for 24 hours at 22° C. Concentrated hydrochloric acid was then used to adjust the pH to 1. The solution was extracted with ethyl acetate 8 times and the organic layer was rinsed with brine and dried over sodium sulfate. The solvent was evaporated to dryness to give 6.5 g of the crude product as a colorless syrup.

Figure 2:
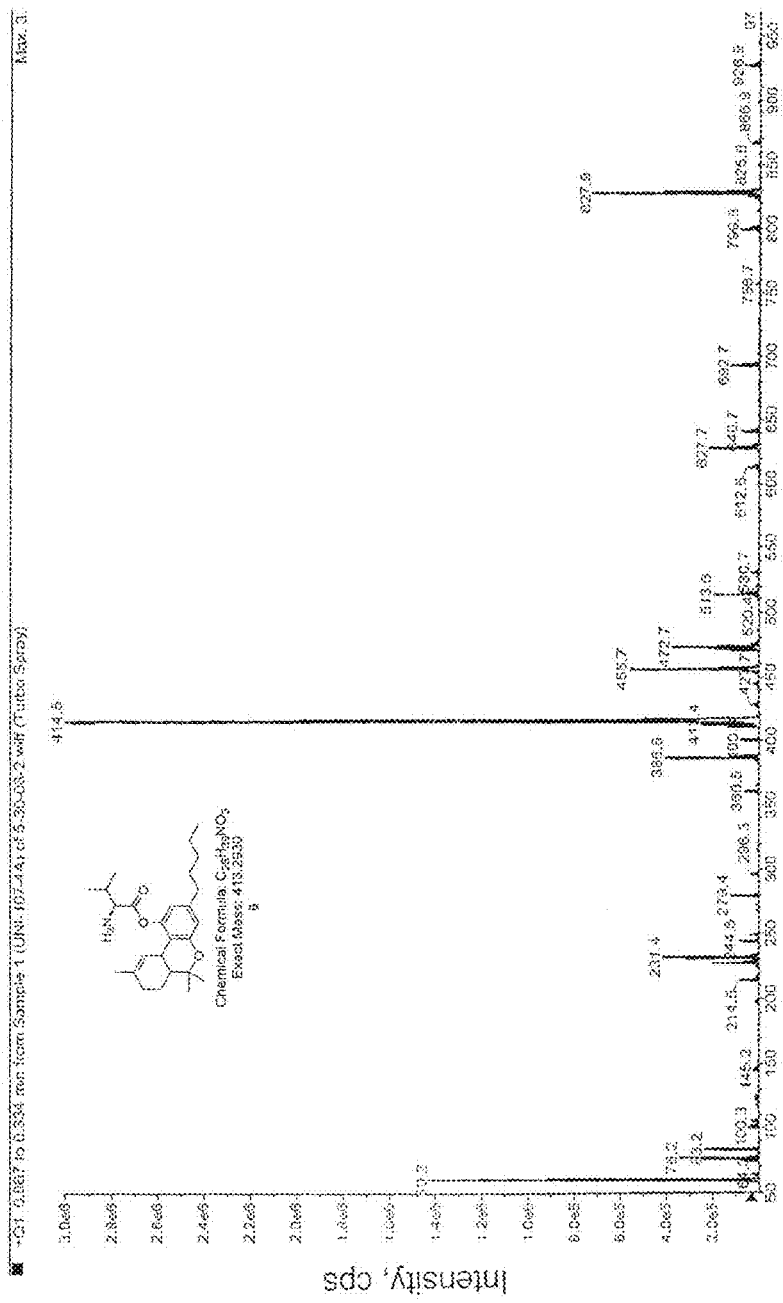
FIG. 2: LC/MS of compound 6 (+ive mode) M+H=414
Figure 3:
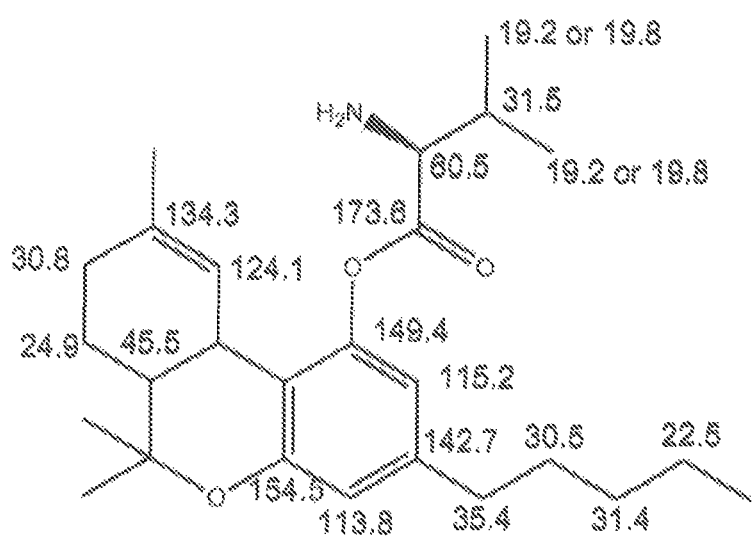
FIG. 3: Representative peaks in carbon spectroscopy for compound 6

A 1.1 equivalent of this product was dissolved in dichloromethane and 1.1 equivalent of DCC was added to it (solution A). $\Delta^9$-THC (1 equivalent) was dissolved in dichloromethane along with a catalytic amount of DMAP (dimethyl amino pyridine) which was added drop-wise to solution A. The reaction mixture was stirred at room temperature for 1 hour and the reaction progress was monitored through TLC. After one hour the reaction mixture was worked up and the product was purified using silica gel column chromatography. Fractions having the product were combined and evaporated to obtain the protected $\Delta^9$-THC-valine ester (95% yield), which was confirmed by mass spectroscopy. The latter was dissolved in dichloromethane and 0.05 mmol of tetrakis(triphenylphosphine) palladium was added along with 0.01 mmol of phenyl silane. The reaction was allowed to stir at room temperature for 30 minutes. The solvent was then evaporated and the product 6 was purified using column chromatography (>87% yield) and confirmed by mass spectroscopy in the positive ionization mode (M+H=414.5) (FIG. 2). The structure of product 6 was also confirmed by spectral analysis $^1$H-NMR and $^{13}$C-NMR (see FIG. 3 for $^{13}$C-NMR assignments).

Figure 4:
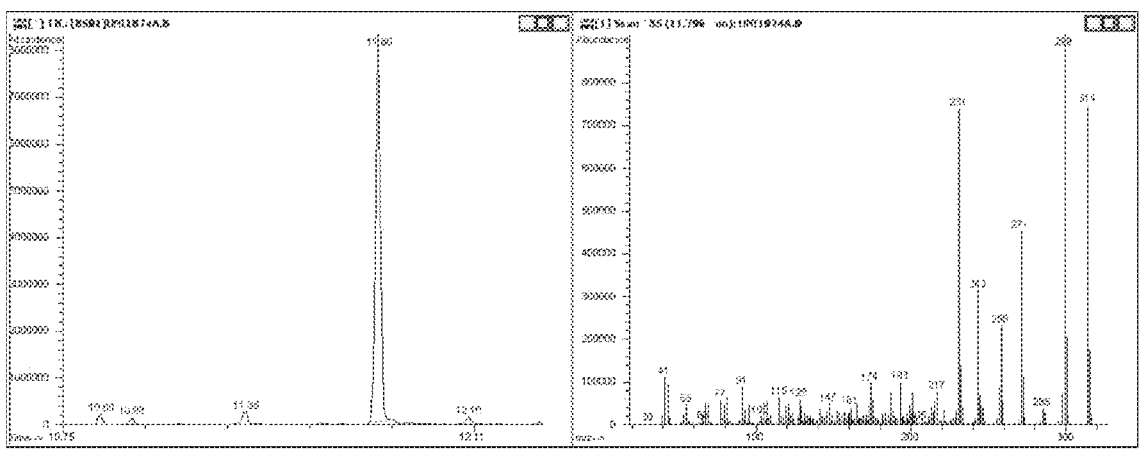
FIG. 4: GC/MS analysis of the hydrolysis product of 6 confirming a $\Delta^9$-THC derivative.

For confirmation that the product 6 is the derivative of $\Delta^9$-THC and not converted to $\Delta^8$-THC, compound 6 was base hydrolyzed followed by GC/MS analysis of the hydrolysis product. The analysis confirmed that it is pure $\Delta^9$-THC as shown in FIG. 4.

Example 2: Preparation of $\Delta^9$-THC-sarcosinate (7)

Figure 5:
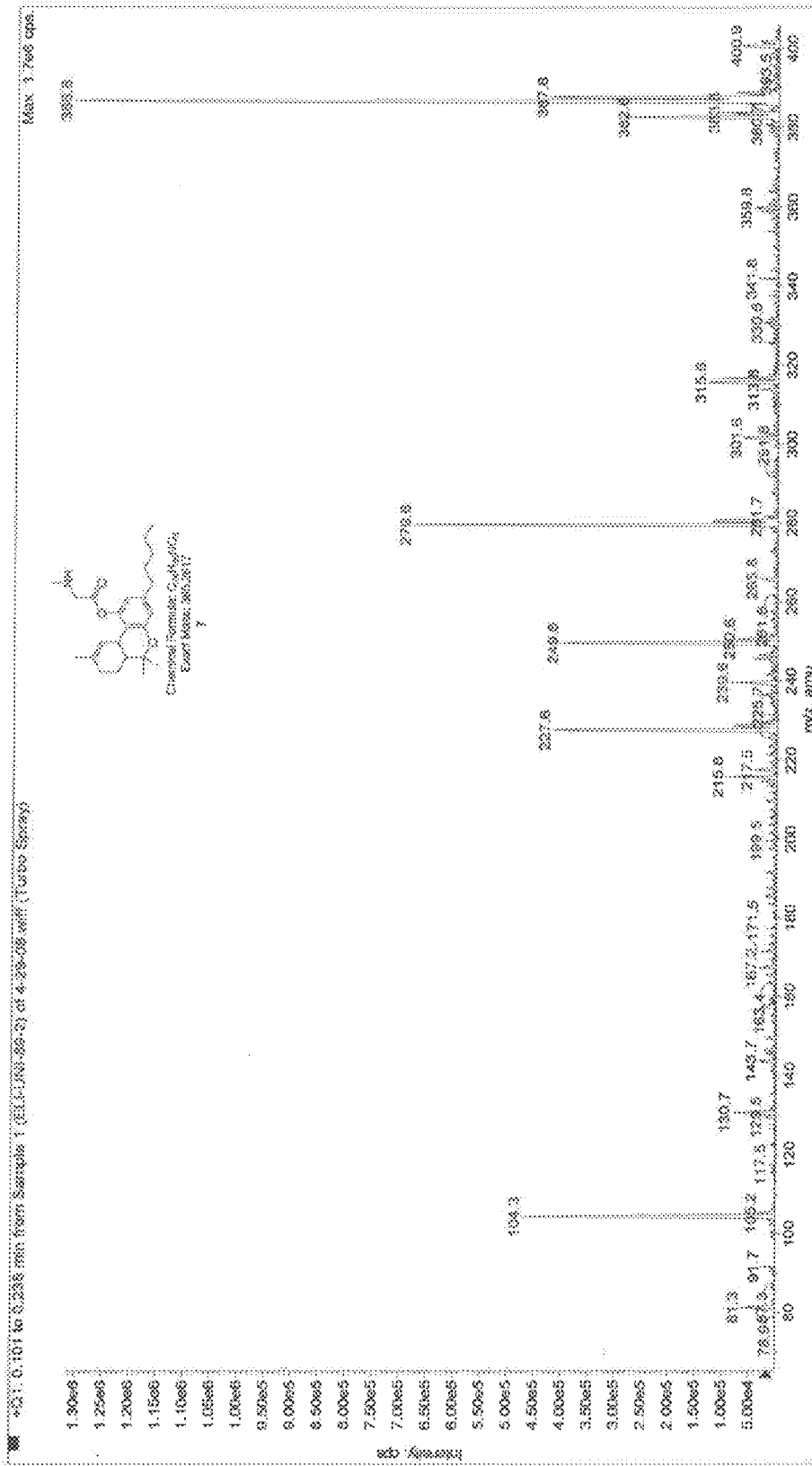
FIG. 5: LC/MS of compound 7 (+ive mode) M+H=386

Following the general procedure outlined in Scheme I, where compound 1 is sarcosine, $\Delta^9$-THC-sarcosinate 7 was synthesized. Product 7 was purified using column chromatography (>80% yield) and confirmed by mass spectroscopy in the positive ionization mode (M+H=386) (FIG. 5). The structure of product 7 was also confirmed by spectral analysis $^1$H-NMR and $^{13}$C-NMR.

Example 3: Preparation of $\Delta^9$-THC-leucinate (8)

Figure 6:
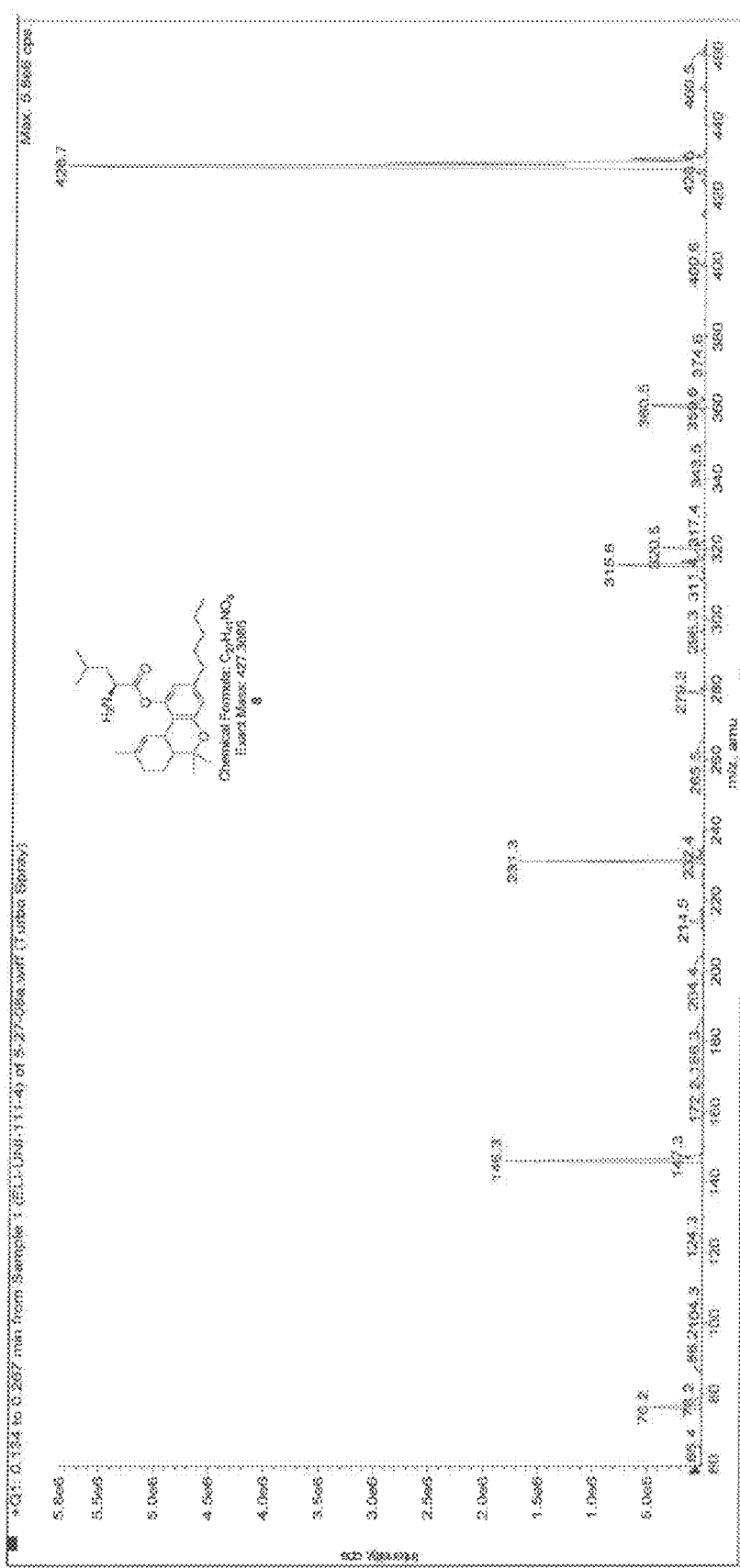
FIG. 6: LC/MS of compound 8 (+ive mode) M+H=428

Following the general procedure outlined in Scheme I, where compound 1 is leucinine, $\Delta^9$-THC-leucinate 8 was synthesized. Product 8 was purified using column chromatography (>81% yield) and confirmed by mass spectroscopy in the positive ionization mode (M+H=428) (FIG. 6). The structure of product 6 was also confirmed by spectral analysis $^1$H-NMR and $^{13}$C-NMR.

Example 4: Preparation of $\Delta^9$-THC-glutaminate (9)

Figure 7:
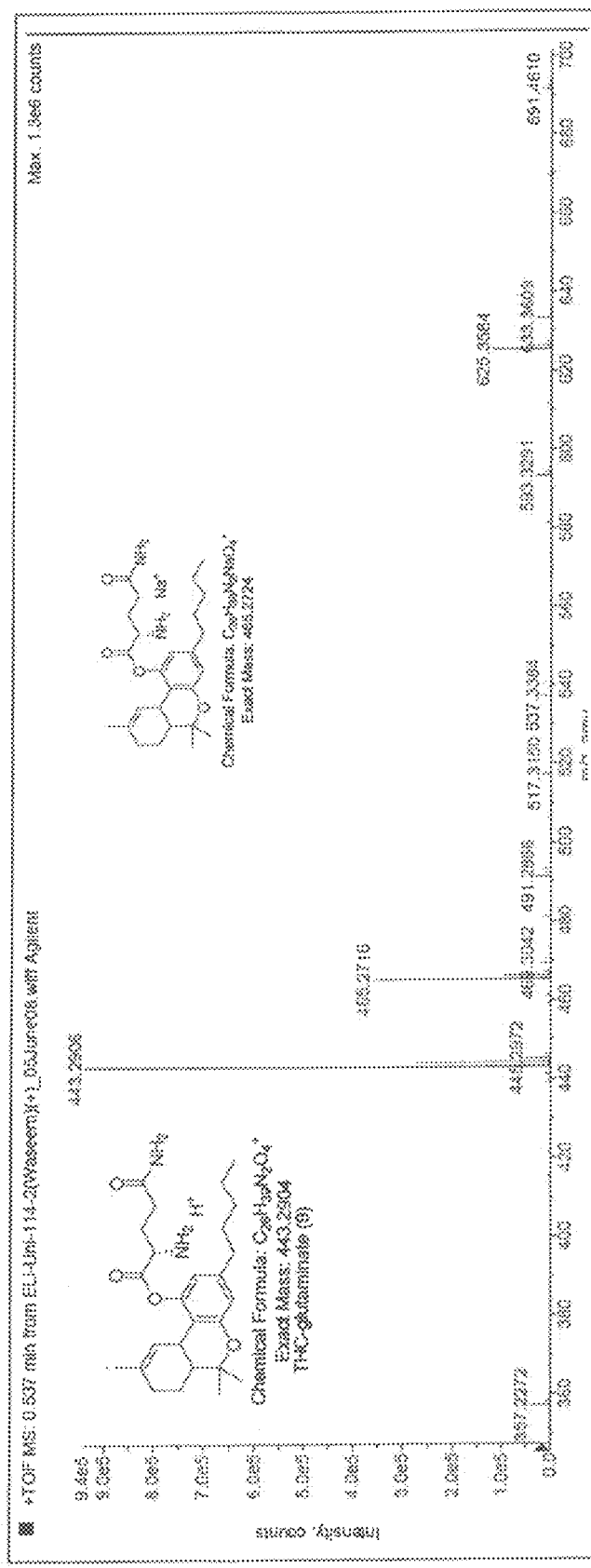
FIG. 7 HREIMS of compound 9 (+ive mode) M+H=443.29 and M+Na=465.27
Figure 8:
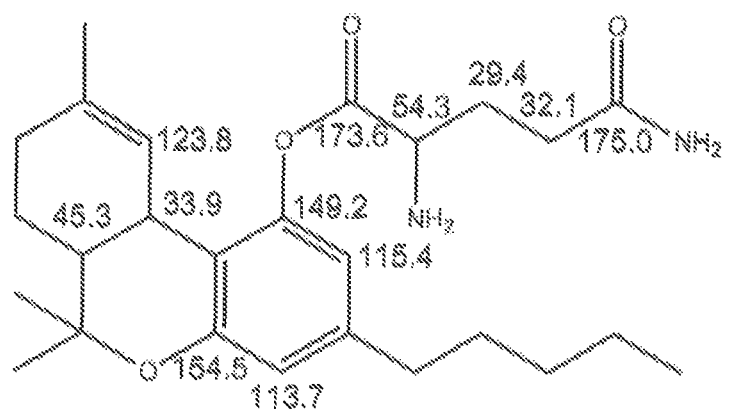
FIG. 8: Representative peaks in carbon spectroscopy for compound 9

Following the general procedure outlined in Scheme I, where compound 1 is glutamine, $\Delta^9$-THC-glutaminate 9 was synthesized. Product 9 was purified using column chromatography (>85% yield) and confirmed by mass spectroscopy in the positive ionization mode (M+H=443) (FIG. 7). The structure of product 9 was also confirmed by spectral analysis ($^1$H-NMR and $^{13}$C-NMR (see FIG. 8 for $^{13}$C-NMR assignments).

Example 5: Preparation of Δ⁹-THC-tryptophinate (10)

Figure 9:
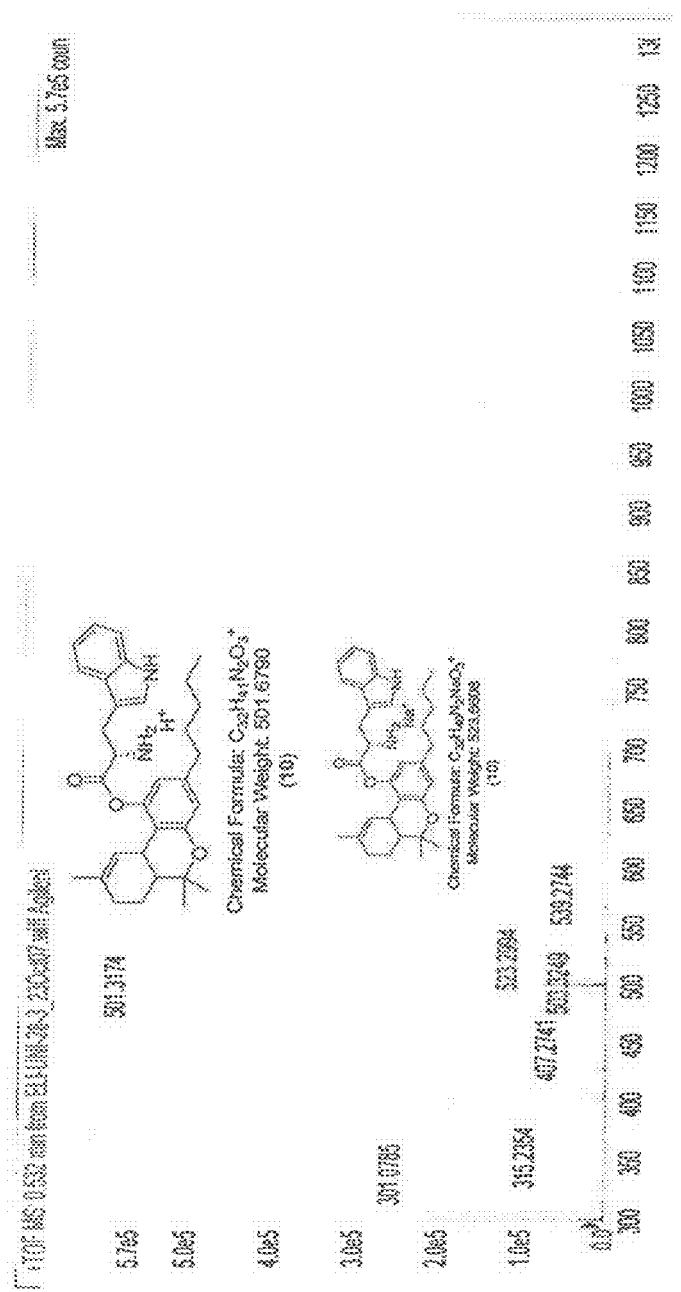
FIG. 9: HREIMS of compound 10 (+ive mode) M+H=501.6, M+Na=523.6 and M+K=539.3
Figure 10:
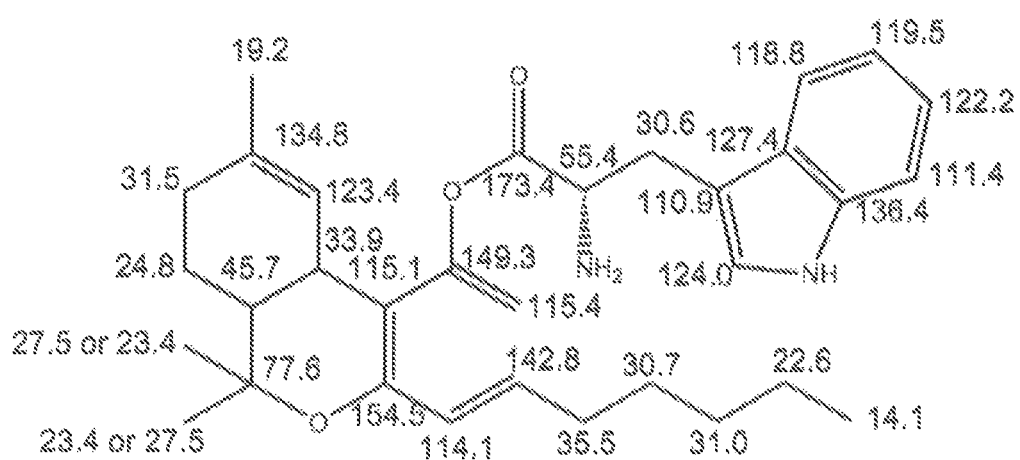
FIG. 10: Representative peaks in carbon spectroscopy for compound 10

Following the general procedure outlined in Scheme I, where compound 1 is tryptophan, Δ⁹-THC-tryptophinate 10 was synthesized. Product 10 was purified using column chromatography (>86% yield) and confirmed by mass spectroscopy in the positive ionization mode (M+H=501) (FIG. 9). The structure of product 10 was also confirmed by spectral analysis ¹H-NMR and ¹³C-NMR (see FIG. 10 for ¹³C-NMR assignments).

Example 6: Preparation of Δ⁹-THC-tyrosinate (11)

Figure 11:
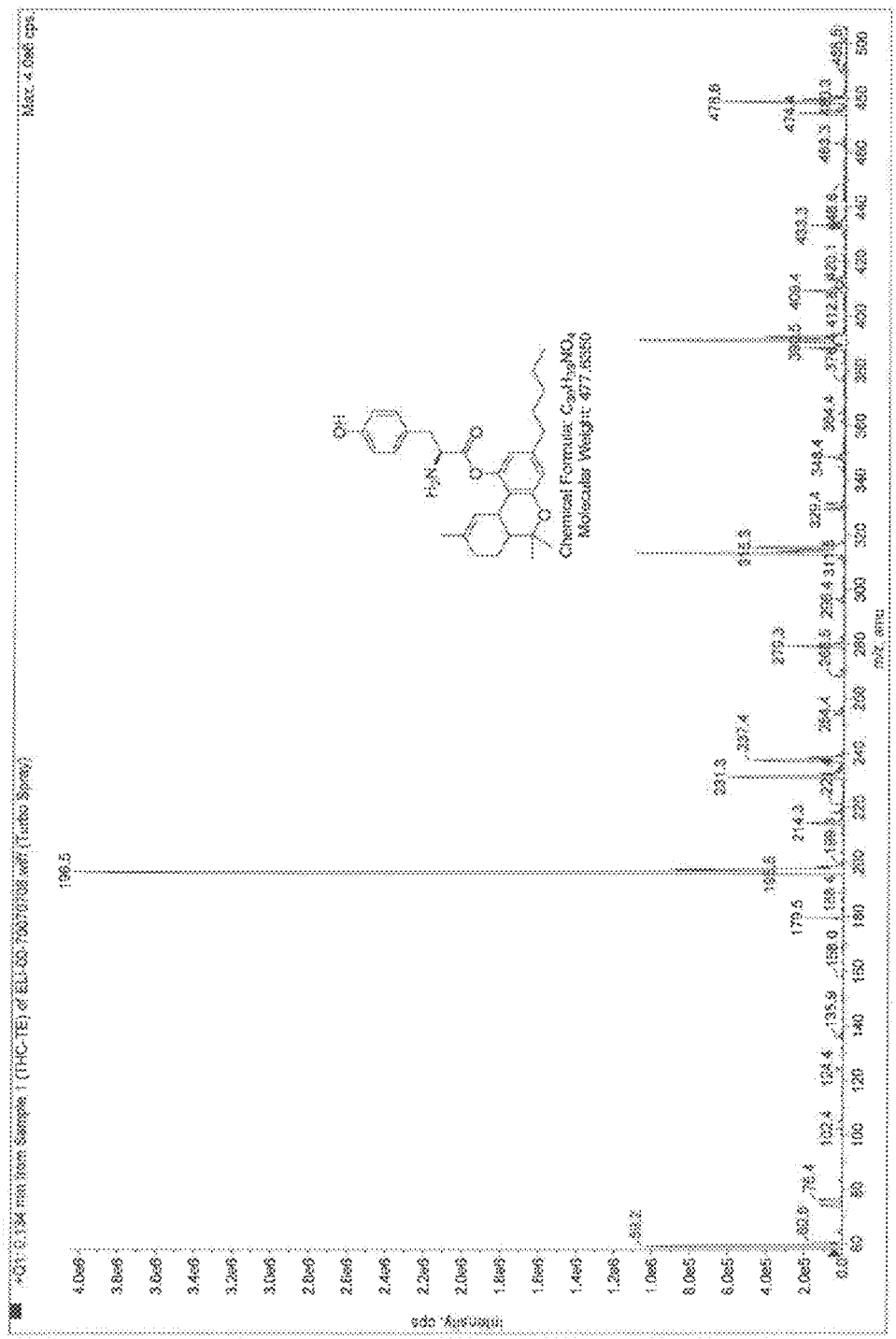
FIG. 11: LC/MS of compound 11 (+ive mode) M+H=478.3

Following the general procedure outlined in Scheme I, where compound 1 is tyrosine, Δ⁹-THC-tyrosinate 11 was synthesized. Product 11 was purified using column chromatography (>82% yield) and confirmed by mass spectroscopy in the positive ionization mode (M+H=478.3) (FIG. 11). The structure of product 10 was also confirmed by spectral analysis ¹H-NMR and ¹³C-NMR.

Example 7: Preparation of Δ⁹-THC-β-alaninate (12)

Figure 12:
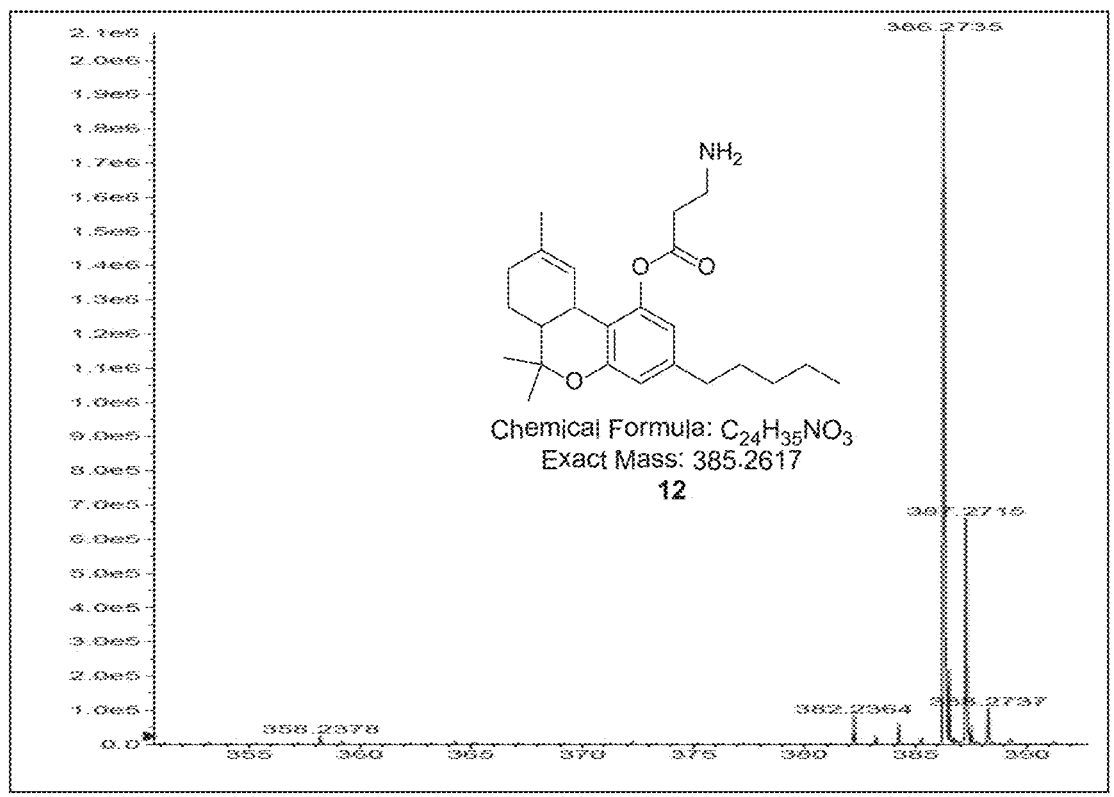
FIG. 12: HREIMS of compound 12 (+ve mode) M+H=

Following the general procedure outlined in Scheme I, where compound 1 is B-alanine, Δ⁹-THC-β-alaninate 12 was synthesized. Product 12 was purified using column chromatography (>82% yield) and confirmed by mass spectroscopy in the positive ionization mode (M+H=386.3) (FIG. 12). The structure of product 6 was also confirmed by spectral analysis ¹H-NMR and ¹³C-NMR.

Example 8: Preparation of Δ⁹-THC-4-(4-aminophenyl)butyrate (12)

Figure 13:
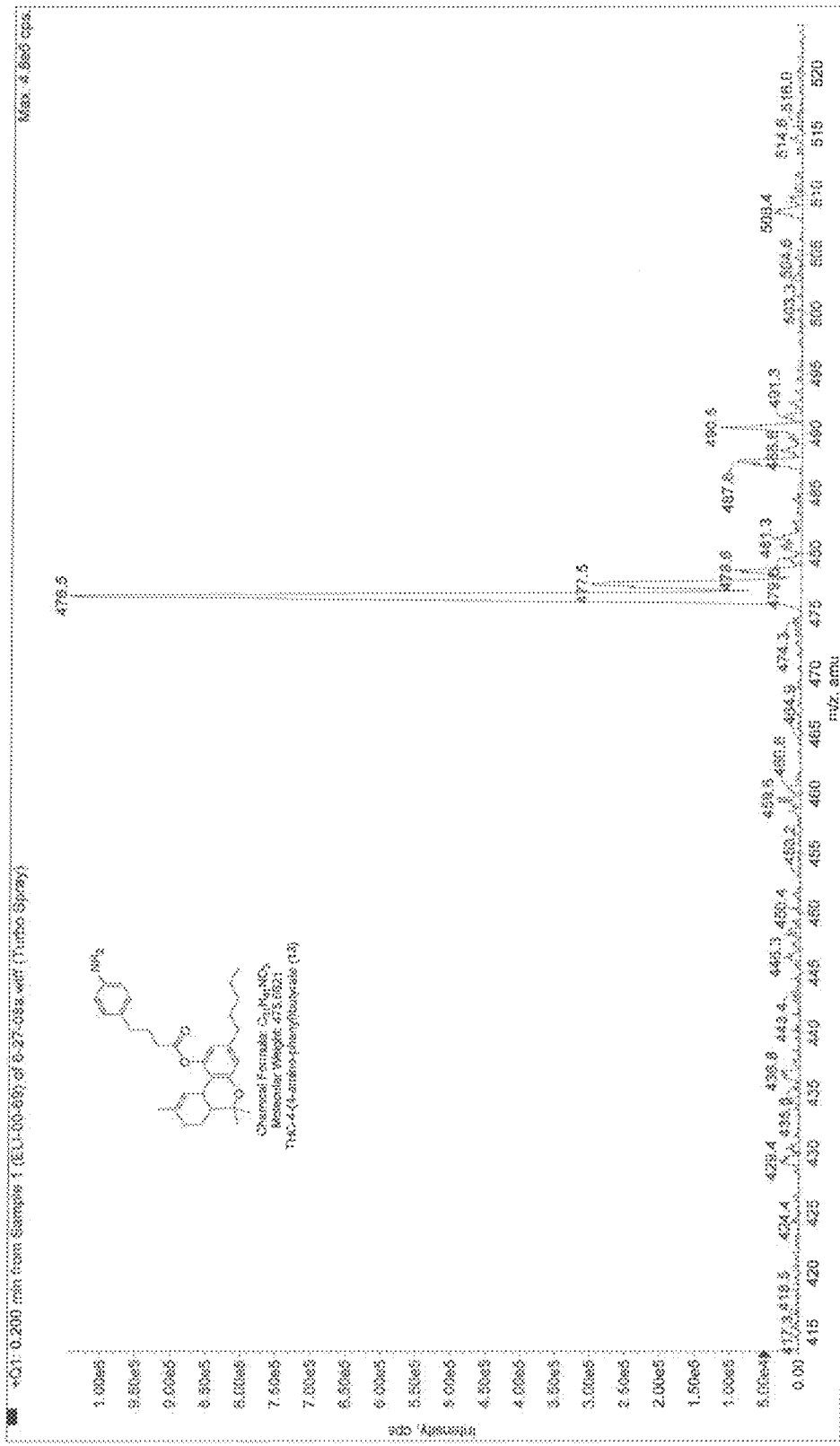
FIG. 13: LCMS of compound 13 (+ive mode) M+H=476
Figure 14:
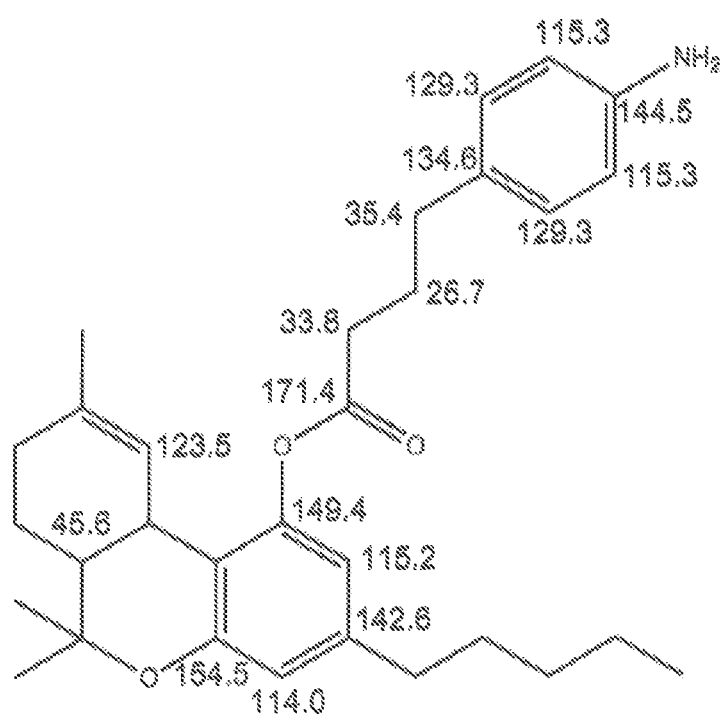
FIG. 14: Representative peaks in carbon spectroscopy for compound 13

Following the general procedure outlined in Scheme I, compound 12 was synthesized, where compound 1 was 4-(4-aminophenyl)butyrate and was used without any protection. Product 12 was purified using column chromatography (>90% yield) and confirmed by mass spectroscopy in the positive ionization mode (M+H=476) (FIG. 13). The structure of product 12 was also confirmed by spectral analysis ¹H-NMR and ¹³C-NMR (see FIG. 14 for ¹³C-NMR assignments).

Scheme II
Scheme for the preparation of THC hemisuccinate derivatives.

Scheme II:

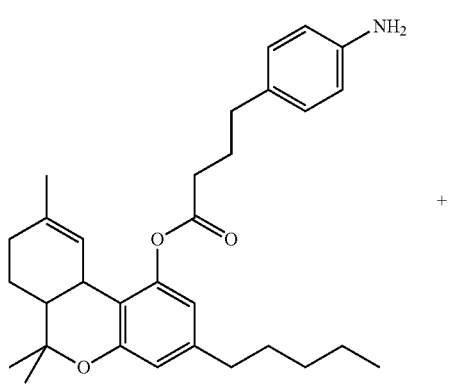

Chemical Formula: $C_{31}H_{41}NO_3$
Molecular Weight: 475.6621
THC-4(4-aminophenyl)butyrate
(13)

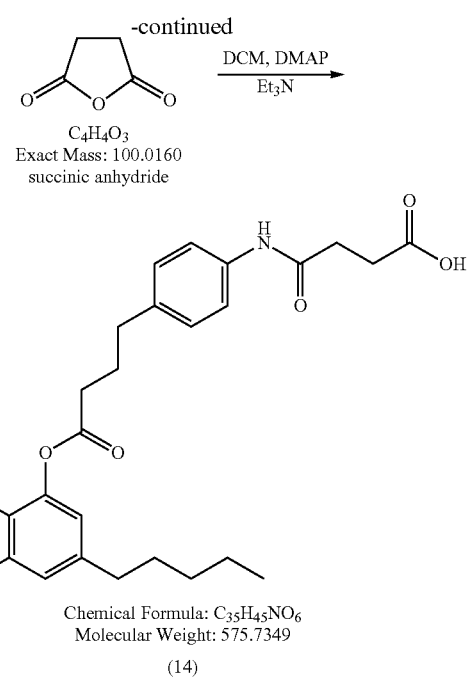

$C_4H_4O_3$
Exact Mass: 100.0160
succinic anhydride

Chemical Formula: $C_{35}H_{45}NO_6$
Molecular Weight: 575.7349
(14)

Example 9: Preparation of THC-4(4-aminophenyl)butyrate-hemisuccinate (14)

THC-4(4-aminophenyl)butyrate (13) was dissolved in 50 mL of dichloromethane and 1.1 eq of succinic anhydride was added along with catalytic amount of DMAP (dimethyl amino pyridine). 1.1 eq. of triethyl amine was added drop wise with a syringe and reaction was allowed to run overnight at room temperature.

In the morning, TLC indicated complete conversion of the starting material to product. Solvent was evaporated up to approximately one third of volume on rotavap, and then 1 mL of DCM was added in it.

A column was packed with silica gel (10 eq.) in DCM and the reaction mixture, which was dissolved in DCM, was loaded at the top of the column. Fractions were collected initially in DCM and then increased to 50% EtOAc. Product came in 40% EtOAc in DCM. Fractions containing pure product were combined and the solvent was evaporated to dryness to get the product (14) (95% yield).

Figure 15:
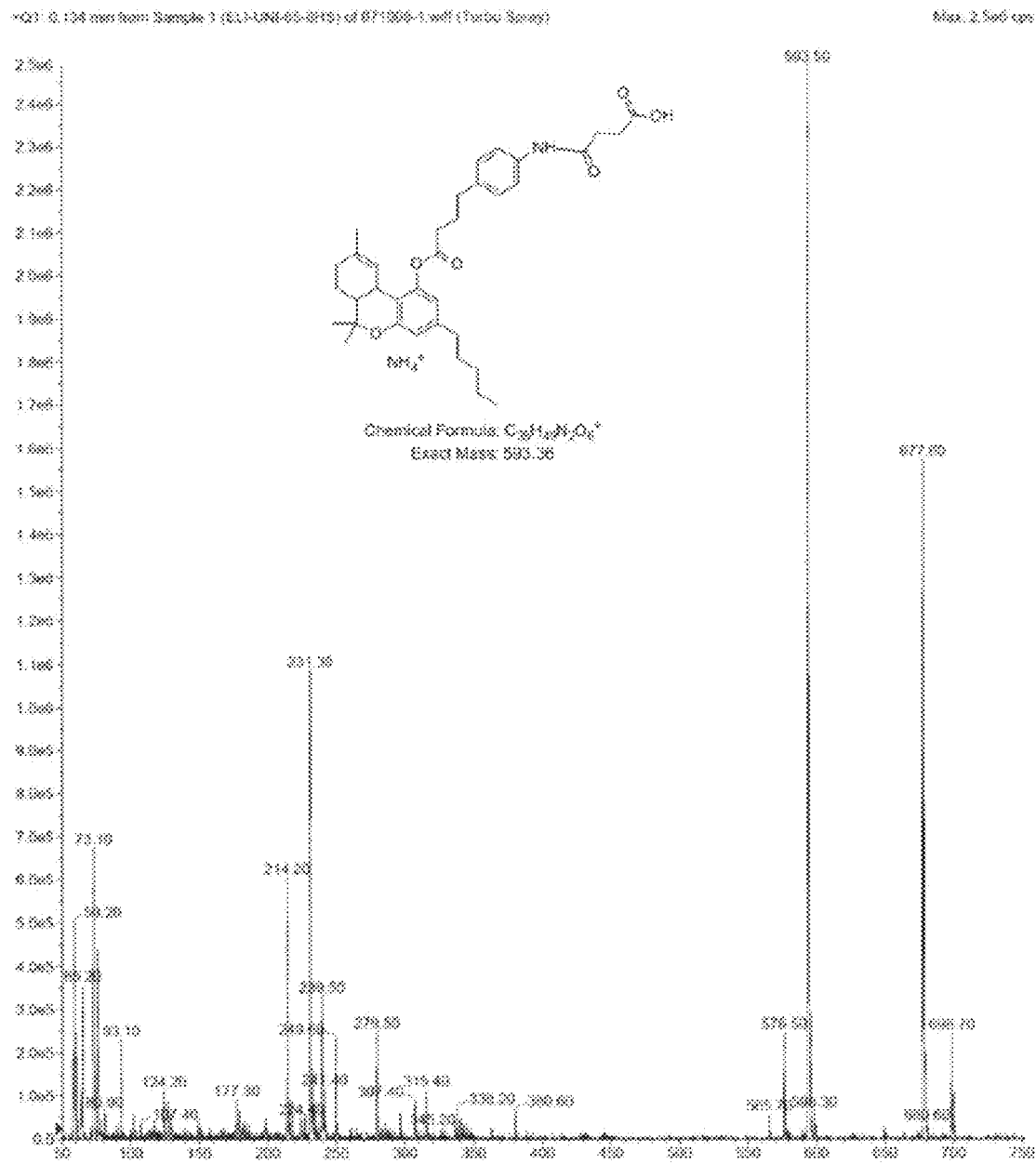
FIG. 15: LCMS of compound 14 (+ive mode) M+NH$_4^+$=593.7
Figure 16:
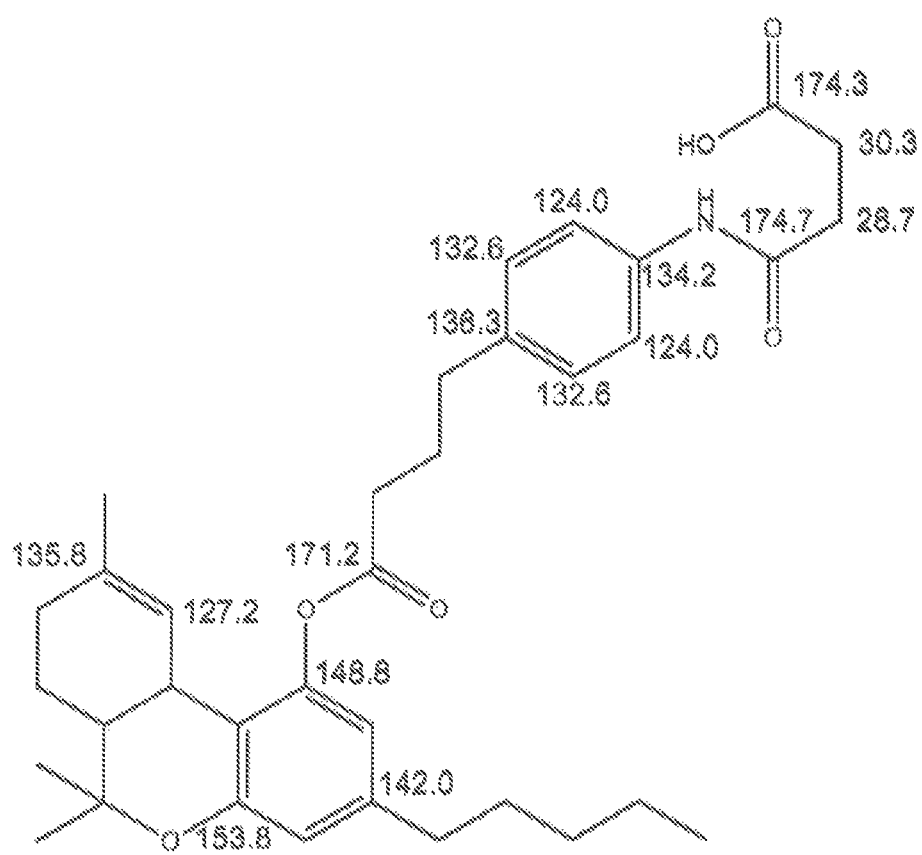
FIG. 16: Representative peaks in carbon spectroscopy for compound 14

Product 14 was confirmed by mass spectroscopy in the positive ionization mode (M+NH₄⁺=593) (FIG. 15). The structure of product 14 was also confirmed by spectral analysis ¹H-NMR and ¹³C-NMR (see FIG. 16 for ¹³C-NMR assignments).

Example 10: Preparation of THC-valinate-hemisuccinate (15)

Figure 17:
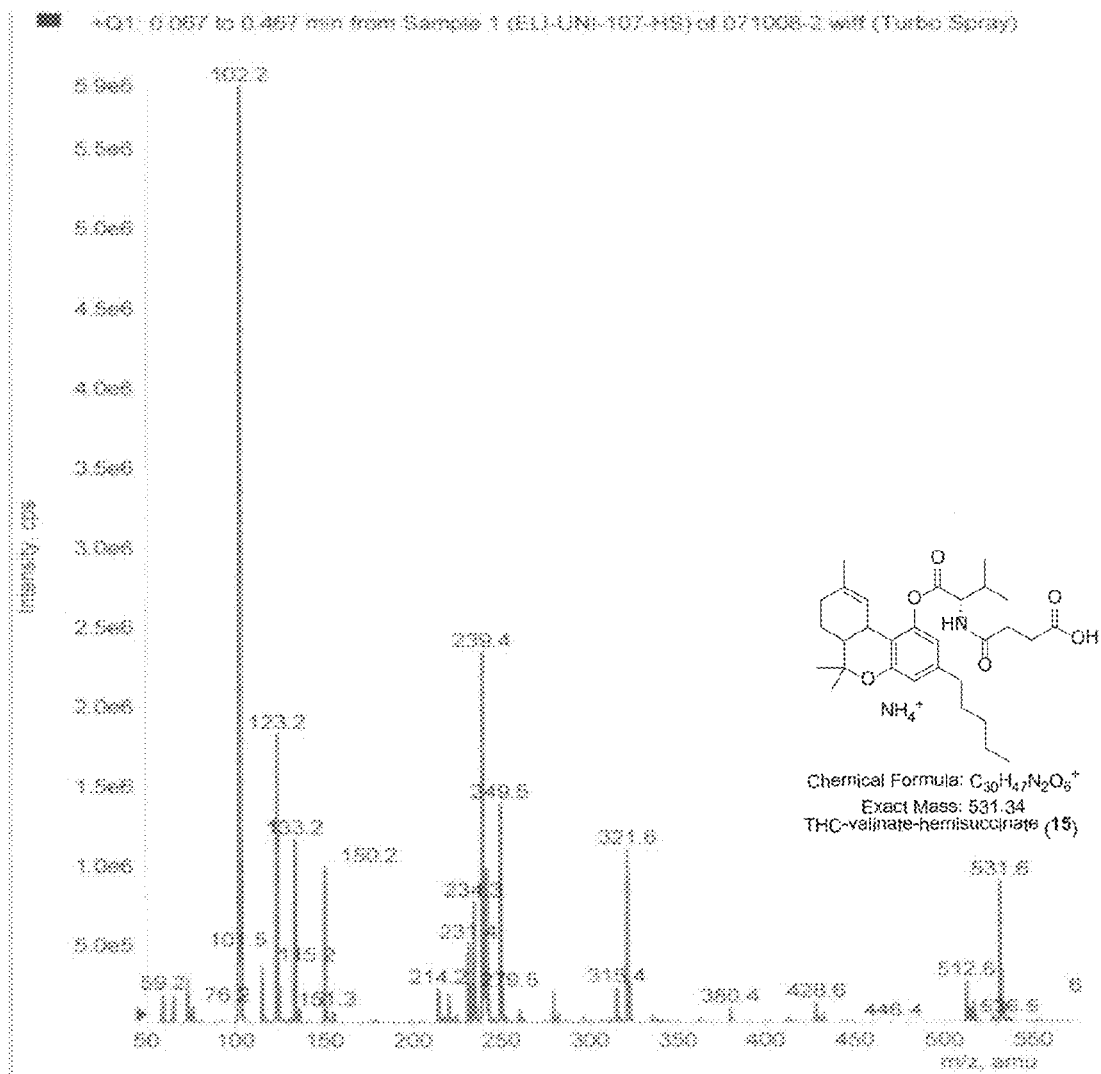
FIG. 17: LCMS of compound 15 (+ive mode) M+NH$_4^+$=531.7
Figure 18:
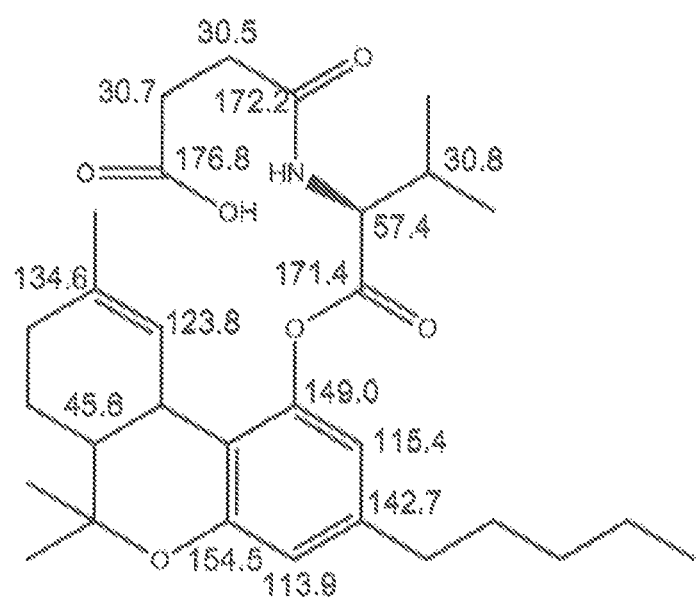
FIG. 18 Representative peaks in carbon spectroscopy for compound 15

Compound 15 was also prepared using scheme II, where the starting material was compound 6 (THC-valinate). Product 15 was purified using column chromatography (>85% yield) and confirmed by mass spectroscopy in the positive ionization mode (M+NH₄⁺=531) (FIG. 17). The structure of product 15 was also confirmed by spectral analysis ¹H-NMR and ¹³C-NMR (see FIG. 18 for ¹³C-NMR assignments).

Spectral analysis of Δ⁹-THC prodrugs prepared above: Identity and purity of the synthesized prodrugs was established by spectral means including ¹H-NMR, ¹³C-NMR and 2D-NMR such as COSY, HMQC, HMBC, as well as other spectroscopic means (IR, UV and MS). The synthetic protocols outlined above yielded prodrugs with ≥95% purity.

Example 11: THC Prodrugs Preformulation Data

A. Solubility a. Aqueous Solubility (μM)

| pH | THC | THC-Sarcosine | THC-Valine | THC-Valine malonate | THC-Valine-HS | THC-Leucine |
|---|---|---|---|---|---|---|
| 1.2 | — | 263.16 ± 75.84 | 78.23 ± 0.66 | 103.61 ± 2.11 | 0.12 ± 0.06 | 21.89 ± 0.26 |
| 2 | 0.95 | 393.89 ± 24.21 | 147.35 ± 24.90 | 228.78 ± 9.79 | 0.17 ± 0.06 | 55.46 ± 0.93 |
| 3 | 2.23 | 250.54 ± 7.38 | 69.78 ± 0.33 | 96.65 ± 3.49 | 0.00 | 12.08 ± 1.40 |
| 4 | 1.27 | 131.70 ± 5.13 | 24.10 ± 1.28 | 26.88 ± 3.01 | 0.00 | 4.33 ± 0.20 |
| 5 | 2.23 | 18.54 ± 1.87 | 3.51 ± 0.62 | 2.36 ± 0.01 | 0.67 ± 0.04 | 0.54 ± 0.06 |
| 6 | 2.23 | 1.38 ± 0.18 | 0.17 ± 0.00 | 0.25 ± 0.04 | 24.80 ± 3.51 | 0.19 ± 0.02 |
| 7 | 2.23 | 0.00 ± 0.00 | 0.00 ± 0.00 | 0.11 ± 0.03 | 303.06 ± 60.72 | 0.00 ± 0.00 |
| 8 | 2.23 | 0.00 ± 0.00 | 0.00 ± 0.00 | 0.12 ± 0.01 | 227.86 ± 21.24 | 0.00 ± 0.00 |
| 9 | — | 0.00 ± 0.00 | 0.00 ± 0.00 | 0.27 ± 0.03 | 0.05 ± 0.00 | 0.00 ± 0.00 |
| Water | 2.23 | 0.00 ± 0.00 | 0.00 ± 0.00 | 2.33 ± 1.19 | 16.54 ± 11.69 | 0.00 ± 0.00 |

| pH | THC-Glutamine | THC-Tyrosine | THC-Tryptophan | THC-Tryptophan Malonate | THC-APB-HS |
|---|---|---|---|---|---|
| 1.2 | 134.25 ± 0.05 | 87.76 ± 4.48 | — | 0.95 ± 0.12 | 0 |
| 2 | 367.06 ± 32.44 | 33.00 ± 1.38 | 0 | 2.81 ± 0.19 | 0 |
| 3 | 104.36 ± 2.55 | 11.06 ± 3.73 | — | 0 | 0 |
| 4 | 50.13 ± 4.97 | 1.52 ± 0.06 | — | 0 | 0 |
| 5 | 12.99 ± 0.04 | 0 | 0 | 0 | 0 |
| 6 | 4.84 ± 0.72 | 0 | — | 0 | 0 |
| 7 | 1.18 ± 0.14 | 0 | 0 | 0 | 64.66 ± 0.97 |
| 8 | 0.76 ± 0.74 | 0 | — | 0 | 110.20 ± 26.12 |
| 9 | 0.35 ± 0.04 | 0 | 0 | 0 | 41.45 ± 7.59 |
| Water | 3.63 ± 1.72 | 0 | 0 | 8.02 ± 8.90 | 0 | b. Aqueous Solubility (μg/ml)

| pH | THC | THC-Sarcosinate (7) | THC-Valinate (6) | THC-Valinate malonate | THC-Valinate-HS (15) | THC-Leucinate (8) |
|---|---|---|---|---|---|---|
| 1.2 | — | 101.38 ± 29.22 | 32.16 ± 0.27 | 53.63 ± 1.09 | 0.06 ± 0.03 | 9.36 ± 0.11 |
| 2 | 0.95 | 151.75 ± 9.33 | 53.66 ± 10.30 | 118.42 ± 5.07 | 0.09 ± 0.03 | 23.71 ± 0.40 |
| 3 | 2.23 | 96.52 ± 2.84 | 28.76 ± 0.14 | 50.03 ± 1.80 | 0.00 | 5.17 ± 0.60 |
| 4 | 1.27 | 50.74 ± 1.98 | 10.34 ± 0.53 | 13.92 ± 1.56 | 0.00 | 1.95 ± 0.09 |
| 5 | 2.23 | 7.14 ± 0.72 | 1.27 ± 0.25 | 1.22 ± 0.00 | 0.35 ± 0.02 | 0.23 ± 0.03 |
| 6 | 2.23 | 0.53 ± 0.07 | 0.07 ± 0.00 | 0.13 ± 0.02 | 12.74 ± 1.80 | 0.08 ± 0.01 |
| 7 | 2.23 | 0.00 | 0.00 | 0.05 ± 0.02 | 155.67 ± 31.19 | 0.00 |
| 8 | 2.23 | 0.00 | 0.00 | 0.06 ± 0.00 | 117.04 ± 10.91 | 0.00 |
| 9 | — | 0.00 | 0.00 | 0.14 ± 0.02 | 0.02 ± 0.00 | 0.00 |
| $H_2O$ | 2.23 | 0.0 | 0.05 | 1.21 ± 0.61 | 8.50 ± 6.00 | 0.0 |

| pH | THC-Glutaminate (9) | THC-Tyrosinate (11) | THC-Tryptophanate (10) | THC-Tryptophanate Malonate | THC-APB-HS (14) |
|---|---|---|---|---|---|
| 1.2 | 59.55 ± 0.02 | 41.92 ± 2.14 | — | 1.58 ± 0.19 | 0.00 |
| 2 | 162.82 ± 14.39 | 15.76 ± 0.66 | 0.00 | 4.65 ± 0.31 | 0.00 |
| 3 | 46.29 ± 1.13 | 5.28 ± 1.78 | — | 0.00 | 0.00 |
| 4 | 22.24 ± 2.20 | 0.73 ± 0.03 | — | 0.00 | 0.00 |
| 5 | 5.76 ± 0.02 | 0.00 | 0.00 | 0.00 | 0.00 |
| 6 | 2.15 ± 0.32 | 0.00 | — | 0.00 | 0.00 |
| 7 | 0.52 ± 0.06 | 0.00 | 0.00 | 0.00 | 37.22 ± 0.56 |
| 8 | 0.34 ± 0.33 | 0.00 | — | 0.00 | 63.45 ± 15.04 |
| 9 | 0.16 ± 0.02 | 0.00 | 0.00 | 0.00 | 23.86± |
| $H_2O$ | 1.61 ± 0.76 | 0.00 | 0.00 | 13.27 ± 14.72 | 0.00 |

B. Chemical Stability pH Dependent at 25° C.

| Medium | THC | THC-Sarcosinate (7) | THC-Valinate (6) | THC-Valinate-HS (15) | First order rate constant (×10⁻³ h⁻¹) THC-Leucinate (8) | THC-Glutaminate (9) | THC-Tyrosinate (11) | THC-Tryptophanate (10) | THC-APB-HS (14) |
|---|---|---|---|---|---|---|---|---|---|
| Buffer pH 5.0 | 17.00 | 38.35 ± 4.32 | 4.06 ± 0.01 | Stable | 15.94 ± 3.38 | 70.23 ± 0.92 | 6.32 ± 3.14 | 8.29 | 3.68 |
| Buffer pH 7.0 | 9.80 | 605.61 ± 125.14 | 47.13 ± 1.16 | Stable | 85.91 ± 16.83 | 153.42 ± 4.26 | 25.02 ± 0.88 | 38.03 | Stable |
| Buffer pH 9.0 | — | 1209.25 ± 203.05 | 67.64 ± 7.67 | Stable | 119.98 ± 33.51 | 756.35 ± 106.61 | 53.88 ± 11.36 | — | Stable |
| Water | — | 25.45 ± 21.99 | 23.70 ± 0.77 | Stable | 8.51 ± 2.80 | 32.72 ± 15.19 | 9.40 ± 0.88 | — | 4.81 ± 0.81 |

C. Thermal Stability—120° C. for 10 min.

| | Drug | Initial, μg (%) | Drug remaining, μg (%) | Drug loading (%) |
|---|---|---|---|---|
| THC | THC | 1280.70 ± 108.77 (100) | 1214.10 ± 39.12 (95.05 ± 5.05) | 85.38 ± 7.25 |
| | CBN | | 56.76 ± 4.86 | 53.85 ± 1.60 |
| THC-Sarcosinate (7) | THC | | 26.68 ± 3.80 | 54.53 ± 3.35 | 79.82 ± 0.85 |
| | CBN | | 40.05 ± 3.45 | 33.83 ± 0.97 |
| | THC-Sarcosinate (7) | 1197.24 ± 12.69 (100) | 841.38 ± 40.18 (70.30 ± 4.10) |
| THC-Valinate (6) | THC | | 61.91 ± 9.49 | 74.35 ± 5.26 | 104.67 ± 2.22 |
| | CBN | | 8.27 ± 1.68 | 8.79 ± 2.43 |
| | THC-Valinate (6) | 1570.09 ± 33.27 (100) | 1440.57 ± 46.34 (91.80 ± 4.90) |
| THC-Leucinate (8) | THC | | −6.13 ± 0.84 | 25.86 ± 0.83 | 103.65 ± 4.12 |
| | CBN | | 16.34 ± 0.50 | 20.27 ± 0.43 |
| | THC-Leucinate (8) | 1554.80 ± 61.76 (100) | 1383.29 ± 40.73 (88.99 ± 0.92) |
| THC-Tyrosinate (11) | THC | | 92.95 ± 3.08 | 123.75 ± 2.69 | 81.51 ± 4.28 |
| | CBN | | 35.68 ± 1.16 | 24.42 ± 0.21 |
| | THC-Tyrosinate (11) | 1222.61 ± 64.25 (100) | 1138.93 ± 60.67 (93.15 ± 0.06) |
| THC-Tryptophanate (10) | THC | | 97.38 ± 6.39 | 96.10 ± 16.64 | 89.84 ± 4.53 |
| | CBN | | 25.59 ± 2.26 | 16.63 ± 2.63 |
| | THC-Tryptophanate (10) | 1347.57 ± 67.93 (100) | 1216.70 ± 32.88 (90.47 ± 7.00) |
| THC-Valinate-HS (15) | THC | | 96.52 ± 3.72 | 80.26 ± 8.59 | 112.21 ± 4.99 |
| | CBN | | 0 | 0 |
| | THC-Valinate-HS (15) | 1411.49 ± 459.10 (100) | 1350.13 ± 387.10 (96.29 ± 3.89) |
| THC-APB-HS (14) | THC | | 0 | 0 | 96.66 ± 2.18 |
| | CBN | | 47.63 ± 9.92 | 38.36 ± 9.70 |
| | THC-APB-HS (14) | 1449.90 ± 32.76 (100) | 1518.84 ± 34.38 (104.81 ± 4.74) |
| THC-Glutaminate (9) | THC | | 0 | 0 | 63.41 ± 2.57 |
| | CBN | | 0 | 0 |
| | THC-Glutaminate (9) | 951.08 ± 38.55 (100) | 721.31 ± 73.76 (75.75 ± 4.69) |
| | THC | | 161.87 ± 3.06 | 189.89 ± 7.16 |
| | CBN | | 32.34 ± 0.69 | 89.43 ± 19.28 |

D. Bioreversion
  a. Plasma Stability

| Drug | Parameters | Porcine Plasma | Rabbit Plasma |
|---|---|---|---|
| THC-Valinate (6) | K (×10⁻² min⁻¹) | 91.16 ± 10.91 | 61.94 ± 6.01 |
| | $T_{1/2}$ (min) | 0.766 ± 0.092 | 1.124 ± 0.109 |
| THC-Sarcosinate (7) | K (×10⁻² min⁻¹) | 63.16 ± 10.44 | — |
| | $T_{1/2}$ (min) | 1.11 ± 0.18 | — |
| THC-Leucinate (8) | K (×10⁻² min⁻¹) | 42.70 ± 3.58 | 33.84 ± 10.92 |
| | $T_{1/2}$ (min) | 1.629 ± 0.137 | 2.160 ± 0.697 |
| THC-Glutaminate (9) | K (×10⁻² min⁻¹) | 53.41 ± 5.84 | — |
| | $T_{1/2}$ (min) | 1.31 ± 0.14 | — |
| THC-Tryptophanate (10) | K (×10⁻² min⁻¹) | 48.55 ± 5.90 | — |
| | $T_{1/2}$ (min) | 1.44 ± 0.17 | — |

-continued

| Drug | Parameters | Porcine Plasma | Rabbit Plasma |
|---|---|---|---|
| THC-Tyrosinate (11) | K ($\times 10^{-2}$ min$^{-1}$) | 93.53 ± 8.79 | — |
| | $T_{1/2}$ (min) | 0.74 ± 0.07 | — |
| THC-APB-HS (14) | K ($\times 10^{-2}$ min$^{-1}$) | Stable | — |
| | $T_{1/2}$ (min) | Stable | — |
| THC-Valinate-HS (15) | K ($\times 10^{-2}$ min$^{-1}$) | 85.54 ± 3.74 | — |
| | $T_{1/2}$ (min) | 8.11 ± 0.35 | — | b. Porcine Buccal Tissue Homogenate Stability

Protein Concentration 2 mg/ml

| Drug | Parameters | Porcine Tissue | Control (IPBS) |
|---|---|---|---|
| THC-Valinate (6) | K ($\times 10^{-3}$ min$^{-1}$) | 16 ± 0.19 | 3.66 ± 0.68 |
| | $T_{1/2}$ (min) | 43.30 ± 0.51 | 192.50 ± 35.62 |
| THC-Sarcosinate (7) | K ($\times 10^{-3}$ min$^{-1}$) | 37.36 ± 3.87 | 23.47 ± 1.60 |
| | $T_{1/2}$ (min) | 18.91 ± 0.4 3 | 29.59 ± 2.01 |
| THC-Leucinate (8) | K ($\times 10^{-3}$ min$^{-1}$) | 22.98 ± 1.49 | 5.49 ± 0.46 |
| | $T_{1/2}$ (min) | 30.21 ± 1.95 | 126.70 ± 10.63 |
| THC-Glutaminate (9) | K ($\times 10^{-3}$ min$^{-1}$) | 40.41 ± 3.30 | 26.30 ± 0.14 |
| | $T_{1/2}$ (min) | 17.21 ± 1.40 | 26.35 ± 0.14 |
| THC-Tryptophanate (10) | K ($\times 10^{-3}$ min$^{-1}$) | 9.06 ± 1.26 | 0.77 ± 0.02 |
| | $T_{1/2}$ (min) | 77.27 ± 10.73 | 903.12 ± 29.55 |
| THC-Tyrosinate (11) | K ($\times 10^{-3}$ min$^{-1}$) | 21.52 ± 0.55 | 1.11 ± 0.04 |
| | $T_{1/2}$ (min) | 32.21 ± 0.81 | 627.59 ± 25.89 |
| THC-Valinate-HS (15) | K ($\times 10^{-3}$ min$^{-1}$) | 2.96 ± 0.19 | 0.40 ± 0.02 |
| | $T_{1/2}$ (min) | 23.43 ± 1.49 | 1663.15 ± 98.62 |

DETAILED DESCRIPTION OF THE PRESENT FORMULATION

Formulations containing $\Delta^9$-THC-amino Acid Esters as Their Hemisuccinate or Hemiglutarate Derivatives, to Effect Bioavailability of $\Delta^9$-THC Through Different Routes of Administration.

A. Suppository Formulations:

$\Delta^9$-THC, the main active cannabinoid in the *cannabis* plant is known to have several beneficial therapeutic activities. The only formulation currently available on the market is an oral preparation containing $\Delta^9$-THC in sesame seed oil with the brand name Marinol®. This formulation suffers from low bioavailability profile and erratic absorption as well as first pass effect which results in the formation high levels of 11-OH-$\Delta^9$-THC with side effects associated with its high psychological activity. Because $\Delta^9$-THC is not absorbed from suppository formulation (or rectal mucosa), we have developed suppository formulation containing the hemisuccinate ester of $\Delta^9$-THC. Although that formulation overcame the problems associated with the oral preparation, the hemisuccinate ester of $\Delta^9$-THC suffered from relative instability, which necessitated formulation in very lipophilic formulation.

The composition in this invention includes a formulation containing the hemisuccinate or hemiglutate derivative of amino acid esters of $\Delta^9$-THC, previously undisclosed. These formulations are exemplified by the preparation of the hemisuccinate derivative of $\Delta^9$-THC-valinate ester, and the obvious significant blood levels obtained after rectal administration of the compound formulated in a suppository preparation using polyethylene glycol 1000 as the base. See example 1 of the formulation section, and FIG. 19.

Figure 20:
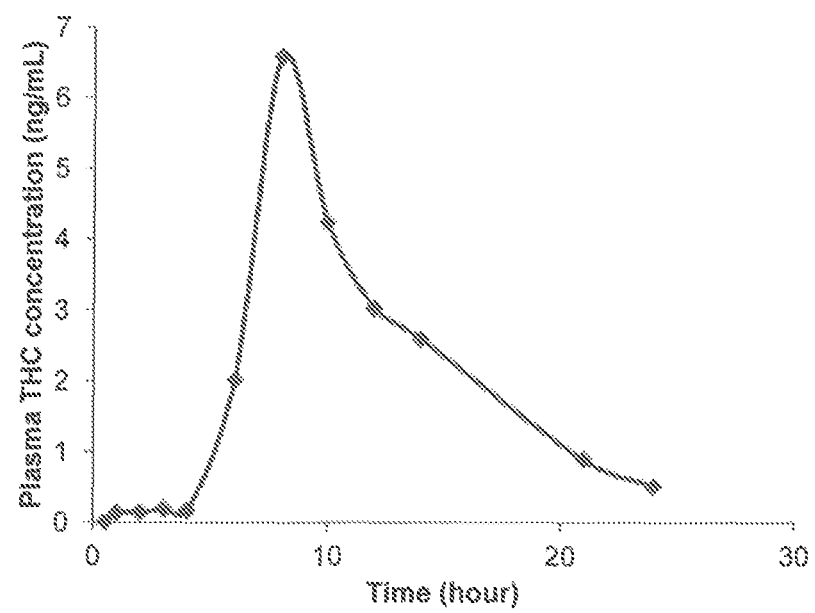
FIG. 20: Plasma THC concentrations as a function of time from THC-Val-HS loaded HME buccal patches. Data represents the mean value from 4 pigs. The animals were maintained under anesthesia for the first 4 hours and were then allowed to come out of anesthesia and given access to food and water.

B. Transmucosal Delivery System Formulations:

Further to the development of the suppositories, this invention involves a transmucosal delivery system effecting bioavailability of $\Delta^9$-THC through the buccal mucosa using compositions of this invention. These formulations (transbuccal or transmucosal) also have the advantage of avoiding the first pass effect and all the problems associated with oral delivery of THC. Hot Melt Extrusion (HME) technology was used to prepare these formulations. HME patches are prepared to contain effective doses of the compounds of this invention. Example 2 of the formulation section shows the preparation and stability of an example of these formulations while example 3 of the formulation section shows the in vivo studies in swine model that demonstrate the bioavailability of THC from transmucosal patches containing THC-Val-HS (FIG. 20). It is important to note that similar patches containing Free (Parent) THC were prepared (table 3 of the formulation section) and tested in vivo and showed no bioavailability from the transmucosal route. Example 4 of the formulation section shows that the blood levels of THC from the buccal preparations (HME patches) is dose dependant.

C. Ophthalmic Formulations for Ocular Delivery of $\Delta^9$-THC for the Treatment of Glaucoma.

Today, there is no ophthalmic preparation on the market available for topical application in the eye that contains $\Delta^9$-THC even though $\Delta^9$-THC is known to lower the intraocular pressure (IOP) when used systemically. That is because $\Delta^9$-THC is very lipophilic compound and therefore does not penetrate through the cornea to reach the inner segments of the eye where it can produce its IOP lowering effects.

The compositions of this invention were formulated in different topical preparations and shown to result in significant levels of $\Delta^9$-THC in the inner segments and tissues of the eye. Furthermore, these formulations were shown to lower the IOP significantly and therefore useful for the treatment of glaucoma.

Examples 5 of the formulation section and 6 of the formulation section show the ocular bioavailability of THC from formulations containing the parent THC vs the formulations of this invention.

Example 1: Bioavailability of $\Delta^9$-THC from a Suppository Formulation Containing the Hemisuccinate Derivative of $\Delta^9$-THC-Valinate THC-Val-HS (41.0 mgs) was dissolved in 40 uL of absolute ethanol. PEG 1000 was weighed (2.5 grams) and added to the vial having THC-Val-HS in ethanol. The vial was sonicated at 40° C., and the material was melted. The vial was vortexed and then sonicated again. While the material was in liquid form, it was pulled into 1 mL syringes.

A cannulated rat was given 100 uL of suppository having 1.64 mgs of THC-Val-HS (equivalent to 1 mg THC). Blood was withdrawn at 0 min, 15 min, 30 min, 1 hr., 2 hr., 4 hr., 6 hr., 8 hr. and 24 hrs. The blood was sonicated at 2000 rpm and the plasma was separated from the cells.

To a 250 uL aliquot of plasma from each time point, 250 uL of 0.1% formic acid in water was added. The solution was vortexed and loaded onto Biotage cartridges with $N_2(g)$. The sample was allowed to adsorb onto the cartridge for 5 min. The sample was then extracted with 2 mL MTBE, 2 mL DCM and 2 mL EtOAc. The solvent was evaporated to 1 mL and vortexed. It was then evaporated to completion and reconstituted in 100 uL ACN for analysis on LC/MS/MS. The curve consisted of 1, 2, 4, 8, 15, 25, 35 and 50 ng/mL.

The LC/MS/MS system consisted of a Shimadzu Prominence HPLC with a dual pump, a vacuum solvent microdegasser, and a controlled-temperature autosampler and a MS/MS detector (Applied Biosystems/MSD Sciex Qtrap3200 with a turbo-ion ESI source operating in positive-ion mode). Specific MRM transitions were monitored for each compound for maximum selectivity and sensitivity. JWH-018 and its metabolites separation was achieved on a Synergi Hydro RP Column (50×3.0 mm; 2.5 u; 100 A) from Phenomenex (Torrance, Calif., USA). The solvent system was composed of solvent A (water with 0.1% formic acid) and solvent B (acetonitrile with 0.1% formic acid) where B was 40% at 3 min., 90% at 3.2 min., and holding it for 2 min., 100% at 6 min., and holding it for 2 min., 40% at 8.5 min. and the run stopped at 15 min. Data acquisition and processing was performed with the Analyst™ 1.5.2 software (Applied Biosystems (AB Sciex), Foster City, Calif.).

Figure 19:
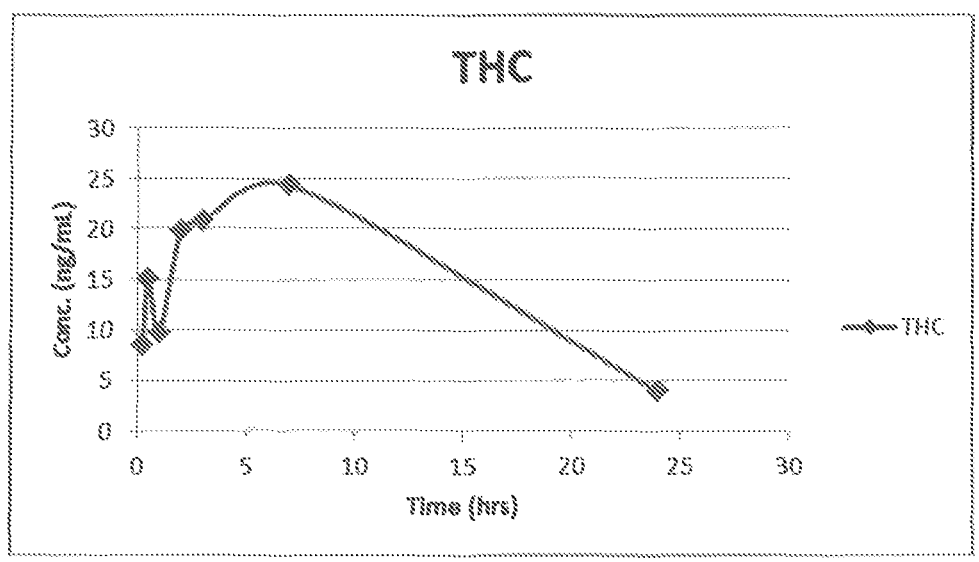
FIG. 19: $\Delta^9$-THC concentration in blood plasma following rectal administration $\Delta^9$-THC-Val-HS in a polyethylene glycol suppository formulation in a dose equivalent to 1 mg $\Delta^9$-THC.

FIG. 19 shows the $\Delta^9$-THC concentration in blood plasma following rectal administration $\Delta^9$-THC-Val-HS in a polyethylene glycol suppository formulation in a dose equivalent to 1 mg $\Delta^9$-THC. FIG. 19: $\Delta^9$-THC concentration in blood plasma following rectal administration $\Delta^9$-THC-Val-HS in a polyethylene glycol suppository formulation in a dose equivalent to 1 mg $\Delta^9$-THC.

Example 2: Preparation and Stability of HME Patches

Representative HME patches containing THC-Val-HS were prepared and stability studies were initiated. The formulations tested and 3 month stability data is provided below in Tables 1 and 2, respectively.

TABLE 1

THC-Val-HS Transmucosal Patch Composition for stability studies.

| Ingredients | Amount (mg) in one patch THC-Val-HS formulation |
|---|---|
| THC-VAL-HS | 9.3* |
| THC | 0 |
| PEO N10 | 159.4 |
| Brij 98 | 6 |
| Sodium deoxycholate | 4 |
| Citric Acid | 2 |
| Vitamin E Succinate | 10 |

*9.3 mg THC-Val-HS is equivalent to 5.7 mg THC

TABLE 2

Three month stability data on the THC-Val-HS Transmucosal Patch. Values indicate mean ± S.D.

| | Assay (as a % of theoretical amount) | | | |
|---|---|---|---|---|
| | | 1 Month | | 3 Month |
| Compound | Initial | 25° C./ 60% RH | 40° C./ 75% RH | 25° C./ 60% RH |
| THC-Val-HS | 108.4 ± 0.2 | 110.6 ± 0.1 | 80.9 ± 3.9 | 108.3 ± 4.6 |

The three month stability data shows that THC-Val-HS is stable in the hot-melt-extruded formulation.

Example 3: In Vivo Studies in the Swine Model Showing Bioavailability of THC from HME Patches Containing THC-Val-HS Formulations prepared for in vivo animal studies are shown in Table 3. THC was used as control formulation. Plasma was sampled from each animal at predetermined times and the amount of THC in the plasma was determined.

TABLE 3

THC-Val-HS Transmucosal Patch Composition for in vivo studies.

| | Amount (mg) in one patch | |
|---|---|---|
| Ingredients | THC-Val-HS formulation | THC formulation |
| THC-VAL-HS | 18.6* | 0 |
| THC | 0 | 10.0 |
| PEO N10 | 159.4 | 168.0 |
| Brij 98 | 6.0 | 6 |
| Sodium deoxycholate | 4.0 | 4.0 |
| Citric Acid | 2.0 | 2.0 |
| Vitamin E Succinate | 10.0 | 10.0 |

*18.6 mg THC-Val-HS is equivalent to 11.4 mg

THC

The Plasma THC Concentration-Time Profile is Shown in FIG. 20.

FIG. 20: Plasma THC concentrations as a function of time from THC-Val-HS loaded HME buccal patches. Data represents the mean value from 4 pigs. The animals were maintained under anesthesia for the first 4 hours and were then allowed to come out of anesthesia and given access to food and water.

Transbuccal systemic bioavailability of THC from the THC patches was extremely poor. No THC levels were detected in the plasma of the swines.

The THC-Val-HS patches however demonstrated significant THC levels in the plasma (FIG. 20). 11-OH-THC or the carboxy metabolite THC-COOH was not seen.

Example 4: Dose Response Curves for Bioavailability of THC from Buccal Mucosa Patches Containing Different Doses of THC-Val-HS A dose dependent plasma concentration time profile was then evaluated. The formulations used are listed in Table 4 and the plasma THC concentration profile is presented in FIG. 21.

TABLE 4

THC-Val-HS Transmucosal Patch Composition for dose dependent studies

| | THC-Val-HS Formulations (amount in mg per patch) | | |
|---|---|---|---|
| Ingredients | THC-Val-HS 5 mg formulation | THC-Val-HS 10 mg formulation | THC-Val-HS 20 mg formulation |
| THC-VAL-HS* | 9.3 | 18.6 | 37.2 |
| PEO N10 | 168.7 | 159.4 | 140.8 |
| Brij 98 | 6.0 | 6.0 | 6.0 |
| Sodium deoxycholate | 4.0 | 4.0 | 4.0 |
| Citric Acid | 2.0 | 2.0 | 2.0 |
| Vitamin E Succinate | 10.0 | 10.0 | 10.0 |

*18.6 mg THC-Val-HS is equivalent to 11.4 mg THC

FIG. 21:

Plasma THC concentrations as a function of time and dose from THC-Val-HS loaded HME patches. Data represents the mean value. The animals for maintained under anesthesia for the first 4 hours and were then allowed to come out of anesthesia and given access to food and water.

Conclusion:

Significant plasma THC levels were observed from the THC-Val-HS loaded transmucosal patch but not from the THC loaded patches.

Example 5: Preparation and Testing of Topical THC Formulations

The following example formulations were evaluated for ophthalmic delivery.

Solution in Mineral Oil (0.1% w/v THC):

An accurately weighed amount of THC was dissolved in light mineral oil, NF, to prepare the mineral oil based formulation.

Emulsion (0.37% w/v THC):

The emulsion formulation consisted of super refined soybean oil (14.0% w/v), oleic acid (6.0% w/v), glycerin (2.25% w/v), poloxamer 188 (2.0% w/v), lipoid E 80 (1.0% w/v), α-tocopherol (0.02% w/v) and deionized water to prepare 20 mL.

Briefly, THC, α-tocopherol and oleic acid were added to super refined soybean oil. Poloxamer and glycerin were added to deionized water. Lipoid E 80 was dispersed in the aqueous phase. Both phases were heated to 70° C. The aqueous phase was added to the oily phase and a coarse emulsion was formed using a high speed homogenizer, Ultra Turrax T25 (IKA®, Wilmington, N.C.). The coarse emulsion was then passed through a high pressure homogenizer Emulsiflex C5 (Avestin®, Ottawa, Canada). The pH of the final emulsion was adjusted to pH 7.4 using sodium hydroxide and the emulsion was filtered through a 0.45 μM membrane filter. The drug loading in the final emulsion was determined by HPLC analysis.

Micellar Solution:

0.125% w/v THC, 0.5% Cremophor RH 40, 0.02% Benzalkonium chloride (BAK), 0.1% ethylenediaminetetraacetic acid (EDTA), 0.5% hydroxypropylmethylcellulose (HPMC, 4000 cps). THC was added to the surfactant solution and allowed to equilibrate at 25° C. for 24 hours and then centrifuged. To the supernatant HPMC, BAK and EDTA were added. Table 5 shows the concentration of THC in the different eye tissues following topical application of these formulations.

Example 6: THC-Valine-Hemisuccinate Formulations

Polymeric Ocular Film:

Hot melt cast method was utilized to prepare the polymeric film. Polyethylene oxide N10 (PEO N10) was used as the matrix forming material. THC-Val-HS was dissolved in acetonitrile and dispersed in polyethylene oxide with adequate mixing. The mixture was placed in a vacuum chamber to evaporate the organic solvent. A 13 mm die was placed over a brass plate and the plate was heated to 70° C. on a hot plate. The drug-polymer mixture was placed in the center of the die, compressed and heated for 2 to 3 minutes. Following cooling, 4 mm×2 mm segments were cut from the film. The final THC-Val-HS concentration in the formulation was 10% w/w.

Cyclodextrin Solution:

THC-Val-HS was dissolved in isotonic phosphate buffered solution (IPBS) containing 2.5% hydroxypropylbeta-cyclodextrin (HPβCD) and 0.5% hydroxypropylmethylcellulose (HPMC 4000 cps). Final THC-Val-HS concentration in the formulation was 0.26% w/v.

Surfactant Solution:

0.1% Cremophor, 0.02% benzalkonium chloride, 0.1% ethylenediamine tetraacetic acid and 0.5% hydroxypropylmethylcellulose. Final concentration was 0.25% w/v. The formulation was prepared as described earlier.

Table 6 shows the concentration of THC in the different eye tissues following topical application of these formulations.

In Vivo Ocular Bioavailability Studies:

In vivo bioavailability of THC from the above formulations were determined in male New Zealand albino rabbits weighing between 2 and 2.5 Kg. Rabbits were anesthetized using a combination of ketamine (35 mg/kg) and xylazine (3.5 mg/kg) injected intramuscularly, and were maintained under anesthesia throughout the experiment. Fifty microliters of the formulations were placed in the cul de sac of the right eye of the anesthetized rabbits.

The polymeric film was placed on the corneo-scleral junction. Ocular irritation was not observed with any of the formulations tested.

The rabbits were euthanized by an overdose of pentobarbital injected through the marginal ear vein after either one or three hours after dosing in accordance with the protocol. The eyes were washed with ice cold IPBS and immediately enucleated and washed again. The ocular tissues were separated, weighed and stored at −80° C. until further analysis. All experiments were carried out in triplicate.

Bio-Analytical Method

Chromatography System:

A Waters 717 plus autosampler, 600E pump controller, 2487 UV detector and an Agilent 3395 integrator was used.

Column: Phenomenex Luna PFP(2) 4.6×250 mm.

Mobile phase consisted of 70% Acetonitrile: 30% water containing 5.05% v/v of o-phosphoric acid at a flow rate of 1 mL/min.

Detector: A Waters 2475 detector was set at an excitation wavelength of 220 nm and THC was detected at emission wavelength of 305 nm. EUFS was set at 150 and gain was set at 50. Injection volume was 50 μL.

Retention time for propofol and THC were 6.9 min and 11.9 min, respectively.

Standard Solutions:

Stock solutions of THC and internal standard (propofol) were prepared in acetonitrile. THC was spiked in blank ocular tissues and allowed to stand for 15 minutes before protein precipitation procedure. Standard curves were prepared for THC in aqueous humor (10 ng-200 ng), vitreous humor (20 ng-200 ng), cornea (20 ng-200 ng), iris ciliary bodies (10 ng-200 ng), retina choroid (10-200 ng) and sclera (20-200 ng). Sample preparation for the various ocular tissues is described as follows.

Aqueous and Vitreous Humor Sample Preparation:

To 100 μL of aqueous humor or 400 μL of vitreous humor 20 μL of drug (10-200 ng) and 20 μL of internal standard (200 ng) prepared in acetonitrile was added. To the aqueous humor and vitreous humor samples 50 μL and 100 μL of 1N sodium hydroxide was added, respectively, and placed at 25° C. At the end of two hours, 50 and 100 μL of 1N HCl (to neutralize the sodium hydroxide) and 200 μL and 400 μL of ice cold acetonitrile (to precipitate the proteins) was added to the aqueous humor and vitreous humor samples, respectively. All samples were centrifuged at 16,000 rpm and taken for analysis.

Preparation of Other Ocular Tissue Samples:

To a weighed amount of the cornea/iris ciliary body/RPE choroid or sclera, 20 μL of drug (20-200 ng) and 20 μL of internal standard (200 ng) in acetonitrile was added followed by 600 μL of ice cold acetonitrile and 100 μL of 1 N NaOH.

The samples were placed at 25° C. and at end of two hours 1N HCl was added. The samples were centrifuged at 16000 rpm for 30 min and taken for analysis.

TABLE 5

Total THC concentrations observed in rabbit ocular tissues 1 h post topical administration of 50 μL of THC in Light Mineral Oil Emulsion or micellar solutions (0.125% w/v THC, 0.5% Cremophor RH 40 + 0.1% EDTA + 0.02% BAK + 0.5% HPMC). Results are depicted as mean ± SD (n = 3).

| Tissue | THC | | |
|---|---|---|---|
| | Light Mineral Oil | Emulsion | 0.5% Cremophor RH 40 + 0.1% EDTA + 0.02% BAK + 0.5% HPMC |
| Drug Concentration in terms of THC (% w/v) | 0.1 | 0.37 | 0.125 |
| Cornea (ng/50 mg Tissue) | 68.8 ± 14.5 | 300.6 ± 79.6 | 553.9 ± 87.4 |
| Aqueous Humor (ng/100 μL) | ND* | ND* | ND* |
| Iris-Cilliary Body (ng/50 mg Tissue) | ND* | ND* | ND* |
| Vitreous Humor (ng/mL) | ND* | ND* | ND* |
| Retina-Choroid (ng/50 mg Tissue) | ND* | ND* | ND* |
| Sclera (ng/250 mg Tissue) | 104.1 ± 36.1 | 171.1 ± 66.6 | 439.3 ± 280.2 |

ND* - Drug concentration below detection limit.

TABLE 6

Total THC concentrations observed in rabbit ocular tissues post topical administration of 50 μL of THC-Val-HS formulations. Results are depicted as mean ± SD (n = 3).

| Tissue | | 2.5% HPβCD + 0.5% HPMC | | 0.1% Cremophor® RH 40 + 0.02% BAK + 0.1% EDTA + 0.5% HPMC | Ocular Film | |
|---|---|---|---|---|---|---|
| | | 1 Hour | 3 Hours | 1 Hour | 1 Hour | 3 Hours |
| Drug Concentration | In terms of THC-Val-HS | 0.26% w/v | | 0.25% w/v | 10% w/w | |
| | In terms of THC-Val-HS | 0.156% w/v | | 0.15% w/v | 6% w/v | |
| Dose (μg) | In terms of THC-Val-HS | 130 | | 125 | 800 | |
| | In terms of THC-Val-HS | 78 | | 75 | 480 | |
| Cornea (ng/50 mg Tissue) | | 1677.1 ± 172.1 | 1142.3 ± 415.9 | 1191.7 ± 231.1 | 1634.5 ± 756.5 | 1043.4 ± 614.4 |
| Aqueous Humor (ng/100 μL) | | 69.4 ± 16.7 | 38.3 ± 10.2 | 62.1 ± 12.6 | 61.3 ± 32.1 | 29.1 ± 14.2 |
| Iris-Cilliary Body (ng/50 mg Tissue) | | 65.8 ± 15.9 | 57.9 ± 16.1 | 51.44 ± 19.5 | 86.03 ± 38.2 | 104.2 ± 41.2 |
| Vitreous Humor (ng/mL) | | ND* | ND* | ND* | ND* | ND* |
| Retina-Choroid (ng/50 mg Tissue) | | ND* | ND* | ND* | 17.02 ± 8.01 | 11.9 ± 4.9 |
| Sclera (ng/250 mg Tissue) | | 882.2 ± 185.8 | 241.8 ± 106.6 | 913.4 ± 432.9 | 1891.2 ± 771.5 | 812.6 ± 501.4 |

ND* - Drug concentration below detection limit.

Conclusion:

The data from tables 5 and 6 show that THC concentrations were not observed in the aqueous humor, iris-ciliary bodies or other inner ocular tissues 1 hour post application of the THC formulations. In contrast, the THC-Val-HS topical formulations performed significantly better, exhibiting significant THC concentrations in the anterior segment ocular tissues at the end of 1 hour. The polymeric film containing THC-Val-HS was able to deliver THC to the retina-choroid also. However, THC levels were below detection limits in the vitreous humor. Significantly, THC concentrations were observed in the anterior segment ocular tissues even after 3 hours post topical application.

Example 7: Pharmacological Evaluation; Effect of Topical Administration of Different Formulations Containing $\Delta^9$-THC or $\Delta^9$-THC-Val-HS Rabbit Glaucoma Model Development:

New Zealand White rabbits were used in a intraocular pressure (IOP) induced model of glaucoma. The rabbits procured from Harlan Laboratories, were first anaesthetized (intramuscular injection of 3.5 mg/kg of Xylazine and 35 mg/kg of Ketamine) followed by a single intravitreal injection of α-chymotrypsin (20 mg/mL, 50 μL, freshly prepared in WFI or buffered saline) using a 30-gauge needle into the right eye. The other eye was used as a control. A drop each of ciprofloxacin, dexamethasone and diclofenac sodium eye drops were instilled, two times a day for five days, to prevent topical inflammation/infection. The eyes were monitored daily for inflammatory symptoms. When the increase in IOP stabilized (constant IOP reading for three successive days; approximately 14 days were needed) the animals were treated with the test formulations. The IOP increased from a baseline of about 20±2 mm Hg and stabilized at around 29±2 mm Hg after about 2 weeks. The animal studies followed UM IACUC approved protocols.

Formulations

THC-Val-HS was selected based on its physicochemical properties and the results of stability studies. Two topical formulations were prepared. One was in Tocrisolve® (emulsion composed of a 1:4 ratio of soya oil/water that is emulsified with the block co-polymer Pluronic® F68) and the other a micellar formulation comprising HPβCD (15% w/v)+Cremophor® RH 40 (0.25% w/v)+BAK (0.01% w/v)+ EDTA (0.1% w/v)+HPMC (0.5% w/v). The Tocrisolve® formulation contained 0.97% w/v THC-Val-HS (0.6% w/v THC) and was prepared by adding THC-Val-HS to Tocrisole™100 and sonicating for 15 minutes. The micellar solution contained 0.89% w/v THC-Val-HS (0.55% w/v THC equivalent) and was prepared as described earlier. This was the maximum amount that could be dissolved in these preliminary solutions. Both formulations were evaluated with respect to their IOP lowering effect in the rabbit glaucoma model.

THC in Tocrisolve® was used as the control. The formulation was prepared by adding THC to Tocrisole™100 and sonicating for 15 minutes.

Figure 22:
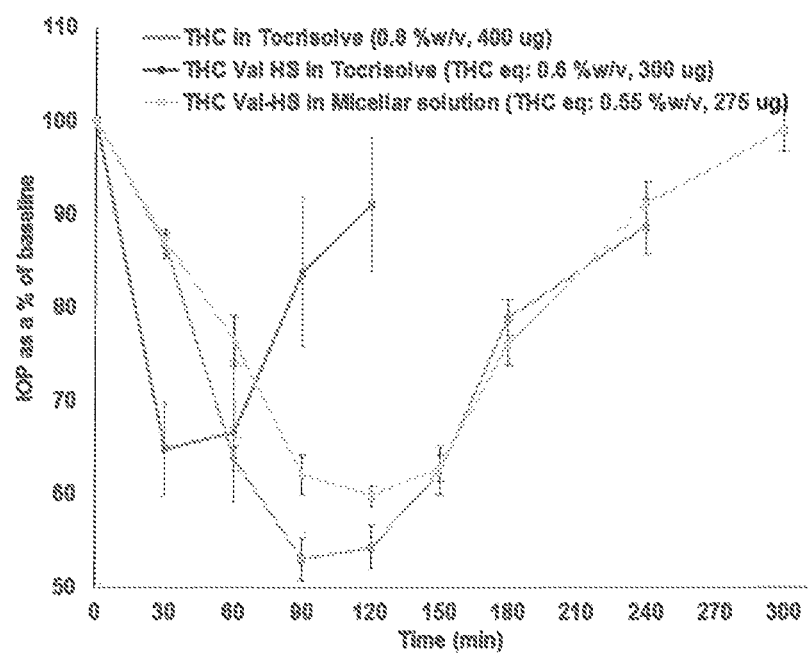
FIG. 22: IOP-Time profile in rabbit glaucoma model (Mean±SEM). The IOP values represent the IOP as a percentage of the baseline IOP.

FIG. 22 IOP-Time profile in rabbit glaucoma model (Mean±SEM). The IOP values represent the IOP as a percentage of the baseline IOP.

Figure 21:
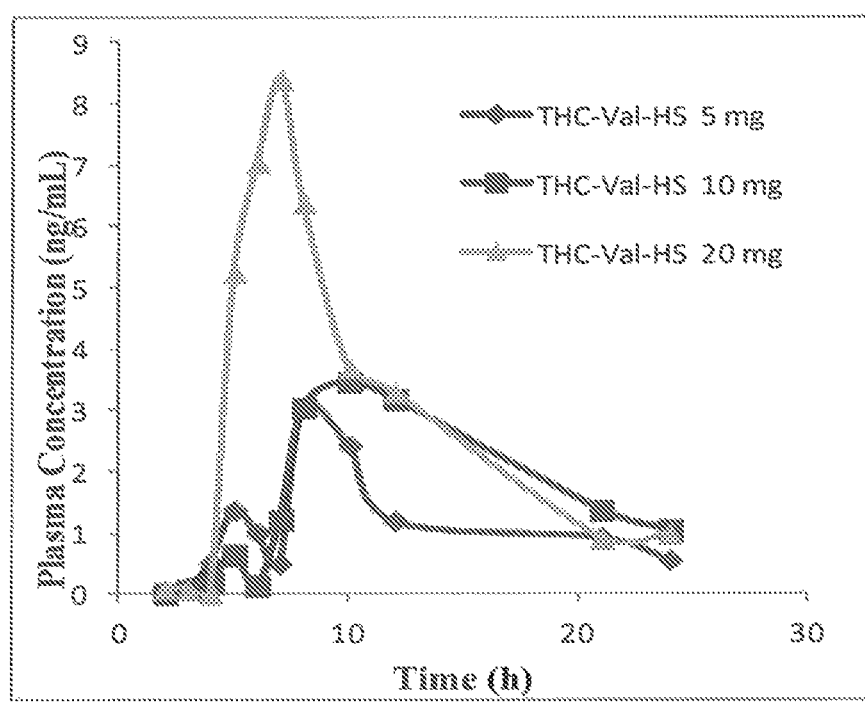
FIG. 21: Plasma THC concentrations as a function of time and dose from THC-Val-HS loaded HME patches. Data represents the mean value. The animals for maintained under anesthesia for the first 4 hours and were then allowed to come out of anesthesia and given access to food and water.

Baseline IOP was measured before instillation of the eye drops and then 50 μL of the formulations were instilled in the cul de sac. IOP was measured every 30 min till IOP (% of baseline) returned to 90% of initial value. THC produced a maximum observed effect of 40% drop in IOP from baseline. The maximum effect was attained within 30 min post topical application (FIG. 21). IOP returned to 90% of baseline within 2 h. Tocrisolve, vehicle, did not affect the IOP.

THC-Val-HS demonstrated a more gradual attainment of peak effect consistent with the fact that pharmacological activity was dependent on the rate of bioreversion of THC-Val-HS to generate THC. Peak IOP drop to 62±3% & 53±3% of the baseline IOP with the micellar solution and Tocrisolve® emulsion, respectively, was attained within 90 min of instilling THC-Val-HS (FIG. 21). Duration of action (time taken for IOP to return to 90% of baseline) with both formulations was about 4 hours. The pharmacological activity was supported by the ocular PK data obtained (Tables I and II).

Conclusions:

The IOP-time profile of the THC-Val-HS treated eyes were significantly better than that of THC, at a lower dose, further supporting the concept that THC-Val-HS was able to improve the penetration and hence delivery of THC into the eye.

What we claim is:

1. A topical ophthalmic formulation for effecting ocular bioavailability of $\Delta^9$-THC and reducing the intraocular pressure in the treatment of glaucoma comprising a therapeutically effective amount of at least one compound of a $\Delta^9$-THC amino ester composition of the formula

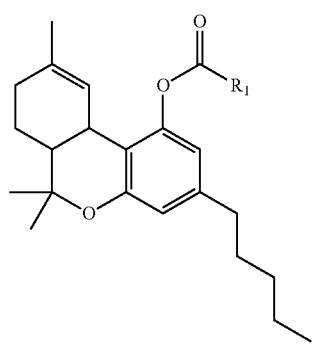

wherein $R_1$ is natural amino acid residue, and salts thereof in an acceptable ophthalmic carrier; and wherein the $\Delta^9$-THC amino ester composition consists essentially of pure $\Delta^9$-THC amino ester, wherein the formulation consists essentially of lipid nanoparticles.

2. A topical ophthalmic formulation for effecting ocular bioavailability of $\Delta^9$-THC and reducing the intraocular pressure in the treatment of glaucoma comprising a therapeutically effective amount of at least one compound of a $\Delta^9$-THC amino ester composition of the formula

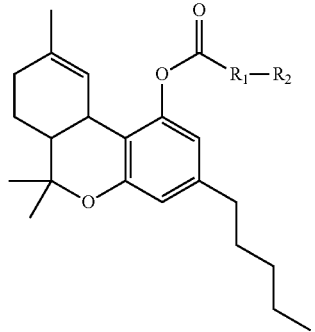

wherein $R_1$ and $R_2$ are residues of natural amino acids, and salts thereof in an acceptable ophthalmic carrier wherein the $\Delta^9$-THC amino ester composition consists essentially of a pure $\Delta^9$-THC amino ester, wherein the formulation consists essentially of lipid nanoparticles.

3. A topical ophthalmic formulation for effecting ocular bioavailability of $\Delta^9$-THC and reducing the intraocular pressure in the treatment of glaucoma comprising a therapeutically effective amount of at least one compound of a $\Delta^9$-THC amino ester composition of the formula

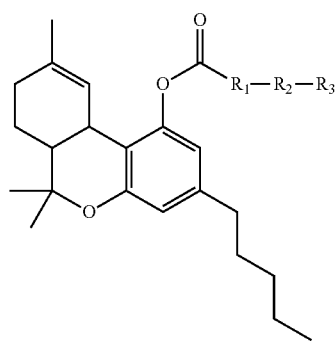

wherein $R_1$, $R_2$ and $R_3$ are residues of natural amino acids, and salts thereof; in an acceptable ophthalmic carrier and wherein the $\Delta^9$-THC amino ester composition consists essentially of a pure $\Delta^9$-THC amino ester, wherein the formulation consists essentially of lipid nanoparticles.

4. The topical ophthalmic formulation for effecting ocular bioavailability of $\Delta^9$-THC and reducing the intraocular pressure in the treatment of glaucoma containing hemisuccinate or hemigluturate derivatives of the $\Delta^9$-THC amino ester compounds of claim 1.

5. The topical ophthalmic formulation for effecting ocular bioavailability of $\Delta^9$-THC and reducing the intraocular pressure in the treatment of glaucoma containing hemisuccinate or hemigluturate derivatives of the $\Delta^9$-THC amino ester compounds of claim 2.

6. The topical ophthalmic formulation for effecting ocular bioavailability of $\Delta^9$-THC and reducing the intraocular pressure in the treatment of glaucoma containing hemisuccinate or hemigluturate derivatives of the $\Delta^9$-THC amino ester compounds of claim 3.

7. The topical ophthalmic formulation according to claim 1, where $R_1$ is valine, sarcosine, leucine, glutamine, tryptophan, tyrosine, or alanine and salts thereof.

8. The topical ophthalmic formulation according to claim 2, where $R_1$ and $R_2$ are valine, sarcosine, leucine, glutamine, tryptophan, tyrosine, or alanine or a combination thereof, and salts thereof.

9. The topical ophthalmic formulation according to claim 3, where $R_1$, $R_2$ and $R_3$ are valine, sarcosine, leucine, glutamine, tryptophan, tyrosine, or alanine or a combination thereof, and salts thereof.

10. A topical ophthalmic formulation for effecting ocular bioavailability of $\Delta^9$-THC and reducing the intraocular pressure in the treatment of glaucoma comprising a therapeutically effective amount of at least one compound of $\Delta^9$-THC amino ester composition of the formula

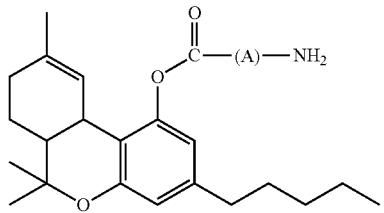

where A is a residue of 1, 2 or 3 natural amino acids, and salts thereof; in an acceptable ophthalmic carrier and wherein the $\Delta^9$-THC amino ester composition consists essentially of a pure $\Delta^9$-THC amino ester, wherein the formulation consists essentially of lipid nanoparticles.

11. The topical ophthalmic formulation according to claim 10, where A is the residue of one natural amino acid and salts thereof.

12. The topical ophthalmic formulation according to claim 10, where A is the residue of two natural amino acids and salts thereof.

13. The topical ophthalmic formulation according to claim 10, where A is the residue of three natural amino acids and salts thereof.

14. The topical ophthalmic formulation according to claim 10 containing hemisuccinate or hemigluturate derivatives of the $\Delta^9$-THC amino ester compounds of claim 10.

15. The topical ophthalmic formulation according to claim 11 containing hemisuccinate or hemigluturate derivatives of the amino ester compounds of claim 11.

16. The topical ophthalmic formulation according to claim 12 containing hemisuccinate or hemigluturate derivatives of the $\Delta^9$-THC amino ester compounds of claim 12.

17. The topical ophthalmic formulation according to claim 13 containing hemisuccinate or hemigluturate derivatives of the $\Delta^9$-THC amino ester compounds of claim 13.

18. The topical ophthalmic formulation according to claim 10 wherein A is valine, sarcosine, leucine, glutamine, tryptophan, tyrosine, or alanine.

19. The topical ophthalmic formulation according to claim 11, wherein A is valine, sarcosine, leucine, glutamine, tryptophan, tyrosine, or alanine.

20. The topical ophthalmic formulation according to claim 12, wherein A is valine, sarcosine, leucine, glutamine, tryptophan, tyrosine, or alanine or a combination thereof.

21. The topical ophthalmic formulation according to claim 13 wherein A is valine, sarcosine, leucine, glutamine, tryptophan, tyrosine, or alanine or a combination thereof.

22. The topical ophthalmic formulation according to claim 1 where $R_1$ is valine and salts thereof.

23. The topical ophthalmic formulation according to claim 1 containing hemisuccinate or hemigluturate derivative of the $\Delta^9$-THC amino ester compound of claim 1.

* * * * *